(12) United States Patent
Del Soldato

(10) Patent No.: US 7,402,600 B2
(45) Date of Patent: Jul. 22, 2008

(54) NITRODERIVATIVES OF CARDIOVASCULAR AGENTS

(75) Inventor: Piero Del Soldato, Milan (IT)

(73) Assignee: NicOx S.A., Sophia Antipolis (FR)

( * ) Notice: Subject to any disclaimer, the term of this patent is extended or adjusted under 35 U.S.C. 154(b) by 327 days.

(21) Appl. No.: 11/234,084

(22) Filed: Sep. 26, 2005

(65) Prior Publication Data

US 2006/0030605 A1 Feb. 9, 2006

Related U.S. Application Data

(62) Division of application No. 09/926,322, filed as application No. PCT/EP00/03239 on Apr. 11, 2000, now Pat. No. 6,987,120.

(30) Foreign Application Priority Data

Apr. 13, 1999 (IT) .............................. MI99A0752

(51) Int. Cl.
*A61K 31/425* (2006.01)
*A61K 31/415* (2006.01)
*C07D 233/00* (2006.01)
*C07D 277/00* (2006.01)

(52) U.S. Cl. .................. 514/365; 514/369; 514/400; 548/188; 548/201; 548/338.1

(58) Field of Classification Search ................ 514/365, 514/369, 400; 548/188, 201, 338.1
See application file for complete search history.

(56) References Cited

FOREIGN PATENT DOCUMENTS

| EP | 0 012 866 | 7/1980 |
|---|---|---|
| EP | 0 549 318 | 6/1993 |
| EP | 0 562 497 | 9/1993 |
| EP | 0 578 494 | 1/1994 |
| JP | 5 39261 | 2/1993 |

OTHER PUBLICATIONS

McCance & Huether: Pathophysiology: The Biologic Basis for Disease in Adults and Children, 48-54, 1998.
McCance & Huether: Pathophysiology: The Biologic Basis for Disease in Adults and Children, 71-77, 1998.
McCance & Huether: Pathophysiology: The Biologic Basis for Disease in Adults and Children, 1025, 1998.
Schwartz "Oxidative Stress During Viral Infection: A Review", Free Radical Biology & Medicine, 21(5), 641-649, 1996.
Silverstein et al., "Misoprostol Reduces Serious Gastrointestinal Complications in Patients with Rheumatoid Arthritis Receiving Nonsteroidal Anti-Inflammatory Drugs", Ann. Intern. Med, 123(4), 241-249, 1995.
Martindale: The Extra Pharmacopoeia; Thirty-first Edition, 73, 1966.
Current Medical Diagnosis & Treatment, 37th Ed., 431 and 794, 1998.

*Primary Examiner*—Barbara P Badio
(74) *Attorney, Agent, or Firm*—Arent Fox LLP

(57) ABSTRACT

Compounds or their salts having general formulas (I) and (II) wherein: s=is an integer equal to 1 or 2, preferably s=2; b0=0 or 1; A is the radical of a drug and is such as to meet the pharmacological tests reported in the description, C and $C_1$ are two bivalent radicals. The precursors of the radicals B and $B_1$ are such as to meet the pharmacological test reported in the description.

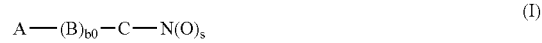
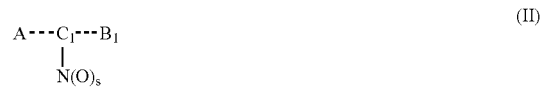

3 Claims, No Drawings

NITRODERIVATIVES OF CARDIOVASCULAR AGENTS

CROSS-REFERENCE TO RELATED APPLICATIONS

This is a divisional of U.S. patent application Ser. No. 09/926,322, filed Oct. 15, 2001, which is now issued as U.S. Pat. No. 6,987,120, and which is the U.S. National Stage of PCT/EP00/03239, filed Apr. 11, 2000, which in turn claims priority to Italian patent application No. MI99A000752, filed Apr. 13, 1999. The contents of all the prior applications are hereby incorporated by reference herein in their entirety.

The present invention relates to new drugs for systemic use and non systemic use, and the composition thereof, to be used in oxidative stress and/or endothelial dysfuntions cases.

By oxidative stress it is meant the generation of free radicals or radicalic compounds, which causes injury both of the cell and that of the surrounding tissue (Pathophysiology: the biological basis for disease in adults and children, McCance & Huether 1998 pages 48-54).

By endothelial dysfunctions it is meant meant those relating to the vasal endothelium. The damage of the vasal endothelium is known as one of those important events that can cause a series of pathological processes affecting various organs and body apparatuses, as described hereinafter (Pathophysiology: The biological basis for disease in adults and children, McCance & Huether 1998 page 1025).

As known, the oxidative stress and/or the endothelial dysfunctions are associated to various pathologies as reported hereinafter. The oxidative stress can also be caused by toxicity of a great variety of drugs, which significantly affects their performances.

Said pathological events are of a chronic, debilitating character and are very often typical of the elderly. As already said, in said pathological conditions the drugs used show a remarkably worsened performance.

Examples of pathological situations caused by the oxidative stress and/or by the endothelial dysfunctions, or present in elderly, are the following:
  For the cardiovascular system: myocardial and vascular ischaemia in general, hypertension, stroke, arteriosclerosis, etc.
  For the connective tissue: rheumatoid arthritis and connected inflammatory diseases, etc.
  For the pulmonary system: asthma and connected inflammatory diseases, etc.
  For the gastrointestinal system: ulcerative and non ulcerative dyspepsias, intestinal inflammatory diseases, etc.
  For the central nervous system: Alzheimer disease, etc.
  For the urogenital system: impotence, incontinence.
  For the cutaneous system: eczema, neurodermatitis, acne.
  The infective diseases in general (ref.: Schwarz-K B, Brady "Oxidative stress during viral infection: A review" Free radical Biol. Med. 21/5, 641-649 1996).

Further the ageing process can be considered as a true pathologic condition (ref. Pathophysiology: the biological basis for disease in adults and children, pages 71-77).

The known drugs when administered to patients having pathologies associated to oxidative stress and/or endothelial dysfunctions, show a lower activity and/or higher toxicity.

This happens for example for drugs such as the antiinflammatory, cardiovascular drugs, respiratory apparatus drugs, central nervous system drugs, bone system drugs, antibiotics, urogenital, endocrine drugs, etc.

Drug research is directed to find new molecules having an improved therapeutic index (efficacy/toxicity ratio) or a lower risk/benefit ratio, also for pathological conditions as those above mentioned, wherein the therapeutic index of a great number of drugs results lowered. In fact in the above mentioned conditions of oxidative stress and/or endothelial dysfunctions, many drugs show a lower activity and/or higher toxicity.

For instance antiinflammatory drugs, such as NSAIDs and anticolitic drugs, such as 5-aminosalicylic acid and its derivatives, show the following drawbacks. NSAIDs result toxic particularly when the organism is debilitated or affected by morbid conditions associated to oxidative stress. Said conditions are for example the following: age, pre-existing ulcer, pre-existing gastric bleeding, debilitating chronic diseases such as in particular those affecting cardiovascular, renal apparatuses, the haematic crasis, etc. ("Misoprostol reduces serious gastrointestinal complications in patients with rheumatoid arthritis receiving non-steroidal anti-inflammatory drugs. A randomized, double blind, placebo-controlled trial." F. E. Silverstein et Al., Ann. Intern. Med. 123/4, 241-9, 1995; Martindale 31a ed. 1996, pag. 73, Current Medical Diagnosis and Treatment 1998, pages 431 and 794).

The administration of anti-inflammatory drugs to patients in the above mentioned pathological conditions can be made only at doses lower than those used in therapy in order to avoid remarkable toxicity phenomena. Thus anti-inflammatory activity results poor.

Beta-blockers, used for the angina, hypertension and cardiac arrhythmia treatment, show side effects towards the respiratory apparatus (dyspnoea, bronchoconstriction), and therefore they can cause problems in patients affected by pathologies to said organs (asthma, bronchitis). Therefore beta-blockers further worsen respiratory diseases such as asthma. Therefore in asthmatic patients doses of said drugs must be used reduced in order not to jeopardize even more the respiratory functionality. Thus the efficacy of the beta-blockers results very reduced.

Antithrombotics, such as for example dipyridamole, aspirin, etc., used for the prophylaxis of thrombotic phenomena, have the same drawbacks. In patients affected by pathologies connected to oxidative stress and/or endothelial dysfunctions, the therapeutic action or the tolerability of these drugs, as in the case of aspirin, is greatly reduced.

Bronchodilators for example salbutamol, etc., are used in the asthma and bronchitis treatment and drugs active on the cholinergic system are used in pathologies such as urinary incontinence. Their administration can produce similar side effects affecting the cardiovascular apparatus, causing problems both to cardiopathic and to hypertensive patients. Cardiopathies and hypertension are pathologies associated, as above said, to the oxidative stress and/or endothelial dysfunctions. Also these drugs show the same drawbacks as those above mentioned.

Expectorant and mucolytic drugs, which are used in the therapy of inflammatory states of the respiratory organs, show drawbacks in patients affected by the above described conditions. Their administration can give rise to heartburn and gastric irritability, particularly in the elderly.

Bone resorption inhibitors, such as diphosphonates (for example alendronate, etc.) are drugs showing high gastrointestinal toxicity. Therefore also these drugs can show the same drawbacks as those above mentioned.

Phosphodiesterase inhibitors, such as for example sildenafil, zaprinast, used in the cardiovascular and respiratory system diseases, are charaterized by similar problems as to tolerability and/or efficacy in the mentioned pathological conditions of oxidative stress and/or endothelial dysfunctions.

Antiallergic drugs, for example cetirizine, montelukast, etc. show similar problems in the mentioned pathological conditions, particularly for that it concerns their efficacy.

Anti-angiotensin drugs, f.i. ACE-inhibitors, for example enalapril, captopril, etc., and receptor inhibitors, for example losartan, etc., are used in the cardiovascular disease treatment. Their drawback is to give side effects to the respiratory apparatus (i.e. cough, etc.) in the above mentioned pathological conditions.

Antidiabetic drugs, both of the insulin-sensitizing and of hypoglycaemizing type, such as for example sulphonylureas, tolbutamide, glypiride, glyclazide, glyburide, nicotinamide etc., are ineffective in the prophylaxis of diabetic complications. Their administration can give side effects, such as for example gastric lesions. These phenomena become more intense in the pathological conditions above mentioned.

Antibiotics, for example ampicillin, clarithromycin, etc., and antiviral drugs, acyclovir, etc., show problems as regards their tolerability, for example they cause gastro-intestinal irritability.

Antitumoral drugs, for example doxorubicine, daunorubicin, cisplatinum, etc., have high toxicity, towards different organs, among which are stomach and intestine. Said toxicity is further worsened in the above mentioned pathologies of oxidative stress and/or endothelial dysfunctions.

Antidementia drugs for example nicotine and colinomimetics, are characterized by a poor tolerability especially in the above mentioned pathologies.

The need was felt to have available drugs showing an improved therapeutic performance, i.e. endowed both of a lower toxicity and/or higher efficacy, so that they could be administered to patients in morbid conditions of oxidative stress and/or endothelial dysfunctions, without showing the drawbacks of the drugs of the prior art.

It has now surprisingly and unexpectedly found that the aforementioned problems evidenced the administration of drugs, to patients affected by oxidative stress and/or endothelial dysfunctions or to the elderly in general, are solved by a novel class of drugs as described hereinafter.

An object of the invention are compounds or their salts having the following general formulas (I) and (II):

$$A\text{-}(B)_{b0}\text{—}C\text{—}N(O)_s \qquad (I)$$

wherein:
s = is an integer equal to 1 or 2, preferably s=2;
$b_0$ = 0 or 1
$A = R\text{-}T_1\text{-}$ wherein
  R is the drug radical and
  $T_1 = (CO)_t$ or $(X)_{t'}$, wherein X=O, S, $NR_{1C}$, $R_{1C}$ is H or a linear or branched alkyl, having from 1 to 5 carbon atoms, or a free valence, t and t' are integers and equal to zero or 1, with the proviso that t=1 when t'=0; t=0 when t'=1;
$B = \text{-}T_B\text{-}X_2\text{-}T_{BI}\text{-}$ wherein
  $T_B$ and $T_{BI}$ are equal or different;
  $T_B = (CO)$ when t=0, $T_B = X$ when t'=0, X being as above defined;
  $T_{BI} = (CO)_{tx}$ or $(X)_{txx}$ wherein tx and txx have the 0 or 1 value; with the proviso that tx=1 when txx=0, and tx=0 when txx=1; X is as above defined;
  $X_2$ is a bivalent bridging group as defined below;
C is the bivalent -$T_C$-Y— radical, wherein
  $T_C = (CO)$ when tx=0, $T_C = X$ when txx=0, X being as above defined;

Y is:

$$\text{—}[C]_{nIX}\text{—}Y^3\text{—}[C]_{nIIX}\text{—O—} \qquad (III)$$

with substituents $R_{TIX}$, $R_{TIX'}$ on first C and $R_{TIIX}$, $R_{TIIX'}$ on second C wherein:
nIX is an integer between 0 and 3, preferably 1;
nIIX is an integer between 1 and 3, preferably 1;
$R_{TIX}$, $R_{TIX'}$, $R_{TIIX}$, $R_{TIIX'}$, equal to or different from each other are H or a linear or branched $C_1$-$C_4$ alkyl; preferably $R_{TIX}$, $R_{TIX'}$, $R_{TIIX}$, $R_{TIIX'}$ are H.
$Y^3$ is a saturated, unsaturated or aromatic heterocyclic ring containing at least one nitrogen atom, preferably one or two nitrogen atoms, said ring having 5 or 6 atoms.
or Y is $Y_0$, selected from the following:
  an alkylenoxy group R'O wherein R' is linear or branched when possible $C_1$-$C_{20}$, preferably having from 1 to 6 carbon atoms, most preferably 2-4, or a cycloalkylene having from 5 to 7 carbon atoms, in the cycloalkylene ring one or more carbon atoms can be replaced by heteroatoms, the ring can have side chains of R' type, R' being as above defined; or —(CH$_2$)$_{n3}$—[phenyl]—(CH$_2$)$_{n3'}$—O— wherein n3 is an integer from 0 to 3 and n3' is an integer from 1 to 3;

[pyridine ring with (CH$_2$)$_{n3'}$—O— and COOH and (CH$_2$)$_{n3}$— substituents]

wherein n3 and n3' have the above mentioned meaning $$(CH_2\text{—}CH\text{—}CH_2\text{—}O)_{nf'}\text{—}$$
with ONO$_2$ substituent $$\text{—}(CH_2\text{—}CH\text{—}CH_2\text{—}O)_{nf'}\text{—}$$
with ONO$_2$ substituent wherein nf' is an integer from 1 to 6 preferably from 1 to 4;

$$\text{—}(CH\text{—}CH_2\text{—}O)_{nf}\text{—} \qquad \text{—}(CH_2\text{—}CH\text{—}O)_{nf}\text{—}$$
with $R_{1f}$ substituent on each wherein $R_{1f}$=H, $CH_3$ and nf is an integer from 1 to 6; preferably from 1 to 4;

preferably Y=—$Y_0$=R'O— wherein R' is as above defined; preferably R' is a $C_1$-$C_6$ alkyl;

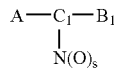 (II)

wherein:

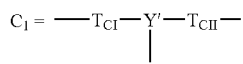

wherein $T_{CI}$ and $T_{CII}$ are equal or different, $T_{CI}$=(CO) when t=0, $T_{CI}$=X when t'=0, X being as above defined;

$T_{CII}$=(CO)$_{tI}$ or (X)$_{tII}$, wherein tI and tII have the 0 or 1 value; with the proviso that tI=1 when tII=0; tI=0 when tII=1; X is as above defined;

Y' is as Y above defined, but with three free valences instead of two, preferably:

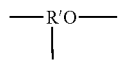

group wherein R' is as above defined, preferably an alkyl from 1 to 6 carbon atoms, most preferably 2-4; or

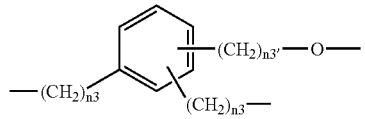

wherein n3 is an integer from 0 to 3 and n3' is an integer from 1 to 3;

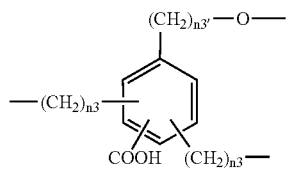

wherein n3 and n3' have the above mentioned meaning;

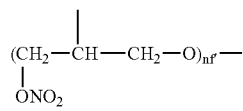

wherein one hydrogen atom on one of the carbon atoms is substituted by a free valence;

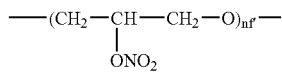

wherein nf' is an integer from 1 to 6 preferably from 1 to 4; wherein one hydrogen atom on one of the carbon atoms is substituted by a free valence;

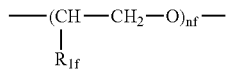

wherein one hydrogen atom on one of the carbon atoms is substituted by a free valence;

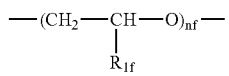

wherein $R_{1f}$=H, $CH_3$ and nf is an integer from 1 to 6; preferably from 1 to 4; wherein one hydrogen atom on one of the carbon atoms is substituted by a free valence;

preferably

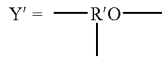

wherein R' is a linear or branched $C_2$-$C_4$, the oxygen which in Y' is covalently linked to the —N(O)$_s$ group is at the end of the free bond indicated in $C_1$ formula;

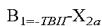

wherein $X_{2a}$ is a monovalent radical as defined below, $T_{BII}$=(CO) when tI=0, $T_{BII}$=X when tII=0, X being as above defined;

$X_2$, bivalent radical, is such that the corresponding precursor of B: -$T_B$-$X_2$-$T_{BI}$- meets test 5 but not test 4, precursor in which the $T_B$ and $T_{BI}$ free valences are each saturated with —OZ, -Z, or with

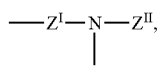

$Z^I$ and $Z^{II}$ being equal or different and have the Z values as defined below, depending on the fact that $T_B$ and/or $T_{BI}$=CO or X, in connection with the values of t, t', tx and txx;

the precursor of C when b0=0 is of -$T_C$-Y—H type wherein the $T_C$ free valence is saturated with —OZ, -Z, or with

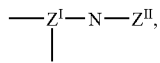

$Z^I$ and $Z^{II}$ being as above defined, meets test 5;

$X_{2a}$ monovalent radical, such that the corresponding precursor of $B_1$-$T_{BII}$-$X_{2a}$ meets test 5 but not test 4, precursor wherein the free valence of $T_{BII}$ is saturated with —OZ, -Z or with

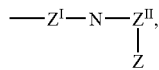

$Z^I$ and $Z^{II}$ being equal or different and having the values as defined below, depending on the fact that $T_{BII}$=CO or X, in connection with the values of tI and tII;

the drug A=R-$T_1$-, wherein the free valence is saturated as indicated hereinafter:

when t'=0 with:

O-Z wherein Z=H or $R_{1a}$, $R_{1a}$ being a linear or when possible branched $C_1$-$C_{10}$ alkyl, preferably $C_1$-$C_5$, or with

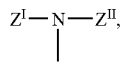

$Z^I$ and $Z^{II}$ being as above defined, when t=0 with -Z, wherein Z is as above defined, with the proviso that the drug is not a steroid, is such as to meet at least one of tests 1-3;

wherein test 1 (NEM) is a test in vivo carried out on four groups of rats (each formed by 10 rats), the controls (two groups) and the treated (two groups) of which one group of the controls and one group of the treated respectively are administered with one dose of 25 mg/kg s.c. of N-ethylmaleimide (NEM), the controls being treated with the carrier and the treated groups with the carrier+ the drug of formula A=R-$T_1$- wherein the free valence is saturated as above indicated, administering the drug at a dose equivalent to the maximum one tolerated by the rats that did not receive NEM, i.e. the highest dose administrable to the animal at which there is no manifest toxicity, i.e. such as to be symptomatologically observable; the drug complies with test 1, i.e. the drug can be used to prepare the compounds of general formula (I) and (II), when the group of rats treated with NEM+carrier+drug shows gastrointestinal damages, or in the group treated with NEM+carrier+drug are observed gastrointestinal damages greater than those of the group treated with the carrier, or of the group treated with the carrier+drug, or of the group treated with the carrier+NEM;

wherein test 2 (CIP) is a test in vitro wherein human endothelial cells from the umbilical vein are harvested under standard conditions, then divided into two groups (each group replicated five times), of which one is treated with a mixture of the drug $10^{-4}$ M concentration in the culture medium, the other group with the carrier; then cumene hydroperoxide (CIP) having a 5 mM concentration in the culture medium is added to each of the two groups; the drug meets test 2, i.e. the drug can be used to prepare the compounds of general formula (I) and (II), if a statistically significant inhibition of the apoptosis (cellular damage) induced by CIP is not obtained with $p<0.01$ with respect to the group treated with the carrier and CIP;

wherein test 3 (L-NAME) is a test in viva carried out on four groups of rats (each group formed by 10 rats) for 4 weeks and receiving drinking water, the controls (two groups) and the treated (two groups), of which one group of the controls and of the treated respectively receives in the above 4 weeks drinking water added of N-ω-nitro-L-arginine methyl ester (L-NAME) at a concentration of 400 mg/litre, the controls in the 4 weeks being administered with the carrier and the treated in the 4 weeks with the carrier+the drug, administering the carrier or the drug+carrier once a day, the drug being administered at the maximum dose tolerated by the group of rats not pretreated with L-NAME, i.e., the highest dose administrable to animals at which no manifest toxicity appears, i.e. such as to be symptomatologically observable; after the said 4 weeks, the water supply is stopped for 24 hours and then sacrified, determining the blood pressure 1 hour before sacrifice, and after sacrifice of the rats determining the plasma glutamic pyruvic transaminase (GPT) after sacrifice, and examining the gastric tissue; the drug meets test 3, i.e. the drug can be used to prepare the compounds of general formula (I) and (II), when in the group of rats treated with L-NAME+carrier+drug, greater hepatic damages (determined as higher values of GPT) and/or gastric and/or cardiovascular damages (determined as higher values of blood-pressure) are found in comparison in comparison respectively with the group treated with the carrier alone, or with the group treated with the carrier+drug, or with the group treated with the carrier+L-NAME;

wherein test 4, which must not be met by the precursors of B or $B_1$ with the free valences saturated as above defined, is the following: it is an analytical determination carried out by adding portions of methanol solutions of the precursor of B or $B_1$ at a $10^{-4}$ M concentration, to a methanol solution of DPPH (2,2-diphenyl-1-picryl hydrazyl-free radical); after having maintained the solution at room temperature away from light for 30 minutes, it is read the absorbance at the wave length of 517 nm of the test solution and of a solution containing only DPPH in the same amount as in the test solution; and then the inhibition induced by the precursor towards the radical production by DPPH is calculated as a percentage by means of the following formula:

$(1-A_S/A_C) \times 100$ wherein $A_S$ and $A_C$ are respectively the absorbance values of the solution containing the test compound+DPPH and that of the solution containing only DPPH.

The criterium for acceptance of the compounds according to this test is the following: test 4 is met by precursor compounds if the inhibition percentage as above defined is higher than or equal to 50%; the precursor of B or $B_1$ must not meet test 4;

wherein test 5 is the following: it is an analytical determination carried out by adding aliquots of $10^{-4}$ M methanol solutions of the precursor of B or $B_1$ or of C=-$T_C$-

Y—H, having the free valence sat-rated as above indicated, to a solution formed by admixing a 2 M solution of desoxyribose in water with 100 mM of phosphate buffer and 1 mM of the salt $Fe^{II}(NH_4)_2(SO_4)_2$; after having 5 hermostatted the solution at 37° C. for one hour, are added, in the order, aliquots of aqueous solutions of trichloroacetic acid 2.8% and of thiobarbituric acid 0.5 M, heating is effected at 100° C. for 15 minutes and the absorbance of the solutions is then read at 532 nm; the inhibition induced by the precursor of B or $B_1$ or $C=-T_C-Y$—H in the confront of radical production by $Fe^{II}$ is calculated as a percentage by means of the following formula:

$$(1-A_S/A_C)\times 100$$

wherein $A_S$ and $A_C$ are respectively the absorbance values of the solution containing the tested compound and the iron salt and that of the solution containing only the iron salt, the compound meets test 5 when the inhibition percentage as above defined of the precursor of B or $B_1$ or $C=-T_C-Y$—H is higher than or equal to 50%;

provided that in the compounds of formula (I) the following drugs under the following conditions are excluded:

when bo=0 and $C=-T_C-Y_0$—, with the free valence of $Y_0$ saturated as above indicated, s=2, the drug of formula $A=R-T_1$-, as above defined, has not to belong to the following classes: drugs for use in incontinence, antithrombotic drugs (ACE-inhibitors), prostaglandins;

when bo=0 and $C=-T_C-Y$—, with the free valence of Y saturated as above indicated, and s=2, the drugs of formula $A=R-T_1$- belonging to the class of non steroid antiinflammatory drugs.

The drugs of the proviso to be excluded, as said, are the following: drugs for use in incontinence as described in the patent application WO 98/09948, antithrombotic drugs (ACE inhibitors) as described in the patent application WO 98/21193, prostaglandin derivatives as described in the patent application WO 98/58910. There are excluded also non steroid antiinflammatory (NSAIDs) as described in WO 95/30641, WO 94/12463, WO 95/09831 respectively.

Preferably the precursor compound of B or $B_1$ (precursor of the $X_2$ or $X_{2a}$ radical in the formulas (I) and (II) respectively), is selected from the following classes of compounds:

Aminoacids: aspartic acid (PI), histidine (PII), 5-hydroxytryptophan (PIII), 4-thiazolidincarboxylic acid (PIV), 2-oxo-4-thiazolidincarboxylic acid (PV)

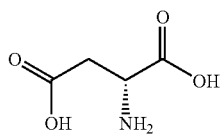

(PI)

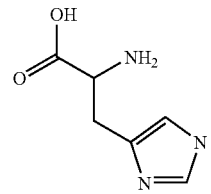

(PII)

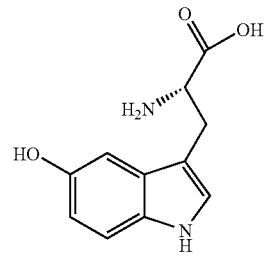

(PIII)

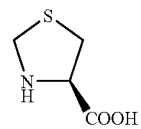

(PIV)

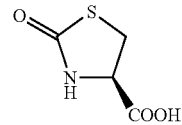

(PV)

mono and polyalcohols or thiols: 2-thiouracil (QI), 2-mercaptoethanol (QII), esperidine (QIII), secalciferol (QIV), 1-α-OH vitamin D2 (QV), flocalcitriol (QVI), 22-oxacalcitriol (QVII), the vitamin D3 derivative esterified with the vitamin A radical (QVIII), the compound of formula (QIX), 24,28-methylene-1α-hydroxyvitamin D2 (QX) the compound derived from 1α,25-dihydroxyvitamin D2 (QXI), 2-mercaptoimidazol (QXII)

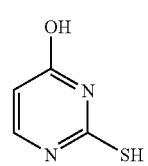

(QI)

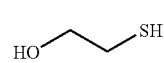

(QII)

(QIII)
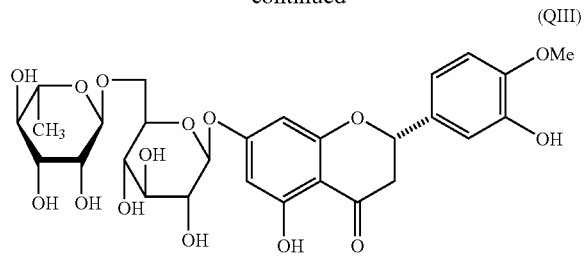
(QIV)
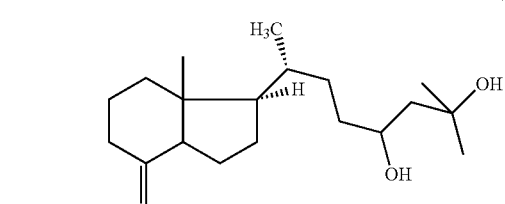
(QV)
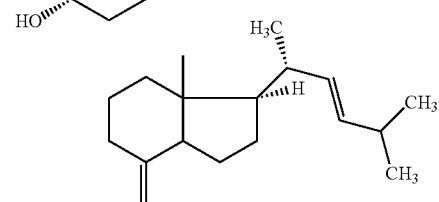
(QVI)
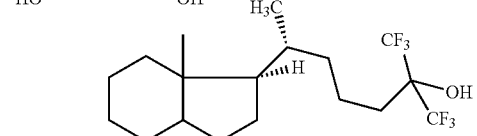
(QVII)
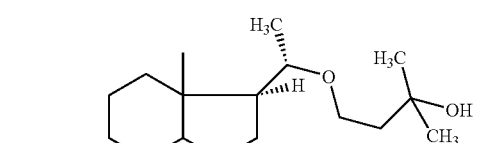
(QVIII)
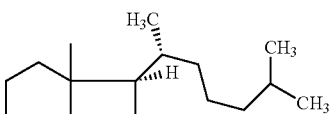
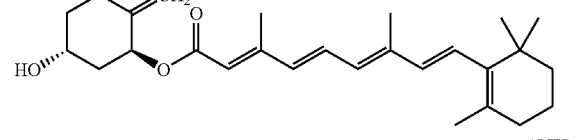
(QIX)
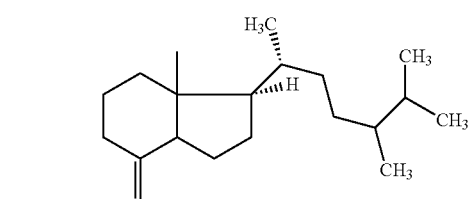
(QX)
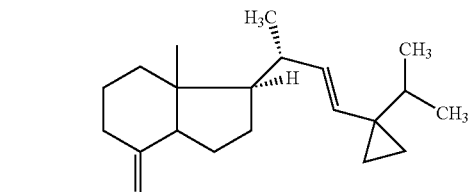
(QXI)
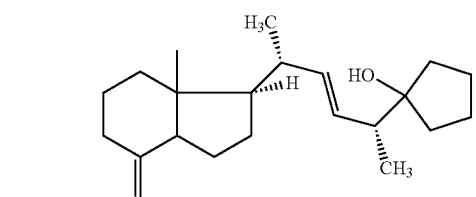
(QXII)
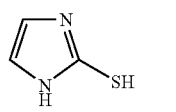

-continued

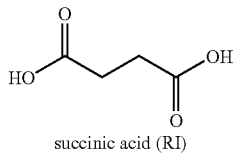

succinic acid (RI)

(RI)

The drug precursor compounds either of B or $B_1$, or of $C=-T_C-Y-H$ are prepared according to the known methods in the prior art, and described for example in "The Merck Index, 12a Ed. (1996), herein incorporated by reference. When available, the corresponding isomers and optical isomers can be used.

The derivative of vitamin D3 with retinoic acid (QVIII) is prepared as described in JP 93039261 (ref. C.A. 119 117617); the compound of formula (QIX) according to EP 562,497; 24,28-methylene-1α-hydroxyvitamin D2 (QX) according to EP 578,494; the derivative compound of dehydroxyvitamin D2 (QXI) according to EP 549,318.

The tests carried out to identify the drug corresponding to the R radical of the formulas (I) and (II) are in detail the following:

Test 1 (NEM): evaluation of the gastrointestinal damage from oxidative stress induced by free radicals formed following administration of N-ethylmaleimide (NEM) (H. G. Utley, F. Bernheim, P. Hochstein "Effects of sulphydril reagents on peroxidation in microsomes" Archiv. Biochem. Biophys. 118, 29-32 1967).

The animals (rats) are distributed in the following groups (no. 10 animals for group):

A) Control Groups:

1° group: treatment: only carrier (aqueous suspension 1% w/v of carboxymethylcellulose, dose: 5 ml/Kg when the drug is administered by os, or a physiologic solution when parenterally administered, i.e. by subcutaneous, intraperitoneal, intravenous or intramuscular route), 2° group: treatment: carrier as above defined+NEM, B) Groups Treated with the Drug:
group I: treatment: carrier+drug,
group II: treatment: carrier+drug+NEM.

The administration routes are those known for the drug, and can be the oral or subcutaneous, intraperitoneal, intravenous or intramuscular route.

The NEM dose is of 25 mg/kg in physiologic solution (sub cutaneous route) and the drug is administered one hour later, in suspension in the carrier, as a single dose which corresponds to the maximum one, or the highest still tolerated by the animals of the group of rats not pretreated with NEM, i.e. the highest administrable dose to said group at which there is no manifest toxicity in the animals, defined as a toxicity that is clearly recognizable for its symptoms. The animals are sacrificed after 24 hours and then one proceeds to the evaluation of the damage to the gastrointestinal mucosa.

The drug meets test 1, i.e. it can be used to prepare the compounds of general formula (I) and (II), when the group of rats treated with NEM+carrier+drug shows gastrointestinal damages, or in said group the gastrointestinal damages noticed are greater than those shown by the group treated with the carrier alone, or the group treated with carrier+drug, or the group treated with carrier+NEM, even though the drug pharmacotherapeutic efficacy, assayed by using specific tests, is not significantly reduced.

Test 2 (CIP): Protection parameter of endothelial cell against the oxidative stress induced by cumene hydroperoxide (CIP).

Human endothelial cells of the umbilical vein are prepared according to an usual standard procedure. Fresh umbilical veins are filled with a 0.1% by weight collagenase solution and incubated at 37° C. for 5 minutes.

Afterwards the veins are perfused with medium M 199 (GIBCO, Grand Island, N.Y.) pH 7.4 further added of other substances, as described in the examples. The cells are collected from the perfusate by centrifugation and harvested in culture flasks T-75, pretreated with human fibronectin. The cells are then harvested in the same medium, further added with 10 ng/ml of bovine hypothalamic growth factor. When the cells of the primary cell culture (i.e. that directly obtained from ex-vivo) form a single layer of confluent cells (about 8,000,000 cells/flask), the culture is stopped and the layers washed and trypsinized. The cellular suspensions are transferred into the wells of a cell culture plate having 24 wells, half of which is then additioned with the same culture medium containing the drug at a $10^{-4}M$ concentration, and harvested in a thermostat at 37° C. at a constant moisture. Only the cells coming from said first sub-cultures are used for the experiments with cumene hydroperoxide (CIP). The cells are identified as endothelial cells by morphological examination and by their specific immunological reaction towards factor VIII; said cultures did not show any contaminations from myocytes or fibroblasts.

Before starting the test, the cellular culture medium is removed and the cellular layers are carefully washed with a physiologic solution at a temperature of 37° C. The wells of the culture plate are then incubated for one hour with CIP at a 5 mM concentration in the culture medium. The evaluation of cellular damage (apoptosis) is carried out by determining the percent variation of the DNA fragmentation with respect to the control group (treated with CIP alone), evaluating the fluorescence variation at the wave length of 405-450 nm. 5 replicates for each sample are carried out.

The drug meets the test, i.e. it can be used for preparing the compounds of general formula (I) and (II), when a statistically significant inhibition of apoptosis (cellular damage) induced by CIP with respect to the group treated with CIP alone is not obtained at $p<0.01$.

Test 3 (L-NAME): evaluation of the endothelial dysfunction induced by administration of L-NAME ($N^W$-nitro-L-arginine-methyl ester) J. Clin. Investigation 90, 278-281, 1992.

The endothelial dysfunction is evaluated by determining the damage to the gastrointestinal mucosa, the hepatic damage and blood hypertension induced by administration of L-NAME.

The animals (rats) are divided in groups as herein below shown. The group receiving L-NAME is treated for 4 weeks with said compound dissolved at a concentration of 400 mg/litre in drinking water. The following groups are constituted (No. 10 animals for group):

A) Control Groups:

1° group: only carrier (aqueous suspension 1% w/v of carboxymethylcellulose, dose: 5 ml/Kg when the drug is administered by os, phisiologic solution when administered parenterally), 2° group: carrier+L-NAME, B) Groups Administered with the Drug:
3° group: carrier+drug,
4° group: carrier+drug+L-NAME.

The administration routes are those known for the drug, and can be the oral or subcutaneous, intraperiteneal, intravenous or intramuscular route. The drug is administered at that dose which results the highest still tolerated by the animals of the group of rats not pretreated with L-NAME, i.e. the highest administrable dose at which there is no evident toxicity in the animals, i.e a toxicity recognizable for its symptoms. The drug is administered once a day for 4 weeks.

At the end of the four weeks treatment access to water is prevented and after 24 hours the animals are sacrificed.

One hour before the sacrifice blood-pressure is determined, and a blood pressure increase is taken as an evaluation of the damage to vascular endothelium. The damage to the gastric mucosa is evaluated as illustrated in test 1 (see example F1). The hepatic damage is determined by evaluation of the glutamic-pyruvic transaminase (GPT increase) after sacrifice.

The drug meets test 3, i.e. it can be used for preparing the compounds of general formula (I) and (II), when in the group of rats treated with L-NAME+drug+carrier it is found an higher hepatic damage (GPT) and/or an higher gastric damage and/or an higher cardiovascular (blood-pressure) damage in comparison to that of the group treated with the carrier alone, or of the group treated wish carrier+drug, or of the group treated with carrier+L-NAME; even if the drug pharmacotherapeutic efficacy, assayed by specific tests, is not significantly reduced.

Under the conditions indicated in the above described in vivo tests 1 and 3 the therapeutic index of the drug is reduced since the usual doses at which the drug can be effective are no longer tolerated.

It has been found by the Applicant that the precursors of B or $B_1$ do not meet test 4 reported hereinafter while they meet, as said, test 5.

Test 4 is a colorimetric test which must not be satisfied by the precursor of B or $B_1$ (precursor of the $X_2$ or $X_{2a}$ of the formulas (I) and (II) respectively). The inhibition of the production of radicals from DPPH (2,2-diphenyl-1-picryl-hydrazyl) is described in M. S. Nenseter et Al., Atheroscler. Thromb. 15, 1338-1344, 1995. 100 μM solutions in methanol of the tested substances are prepared, and an aliquot of each of said solutions is added to a DPPH solution in methanol 0.1 M. After having stored the solutions at room temperature away from light for 30 minutes, their absorbances are read at the wave length of 517 nm, together with that of the corresponding DPPH solution at the same concentration. The absorbance decrease with respect to that of the solution of DPPH at the same concentration of the test solutions is determined. The effectiveness of the tested compound in inhibiting formation of radicals by DPPH is expressed by the following formula:

$$(1-A_S/A_C) \times 100$$

wherein $A_S$ and $A_C$ are respectively the absorbance values of the solution containing the test compound together with DPPH and of the solution containing only DPPH. Test 4 is satisfied when the inhibition is equal or greater than 50%.

Test 5 is a calorimetric test wherein 0.1 ml aliquots of $10^{-4}$ M methanolic solutions of the tested products are added to test tubes containing a solution formed by 0.2 ml of 2 mM desoxyribose, 0.4 ml of phosphate buffer pH 7.4 100 mM and 0.1 ml of 1 mM $Fe^{II}(NH_4)_2(SO_4)_2$ in 2 mM HCl. The test tubes are then maintained at 37° C. for one hour. Then in each test tube 0.5 ml of a 2.8% solution in water of trichloroacetic acid and 0.5 ml of an aqueous 0.1 M solution of thiobarbituric acid are added, in the order. A reference blank is formed by adding to a test tube containing only the above described aqueous solution of reactants 0.1 ml of methanol. The test tubes are closed and heated in an oil bath at 100° C. for 15 minutes. A pink coloration is developed the intensity of which is proportional to the quantity of desoxyribose undergone to radical oxidative degradation. The solutions are cooled at room temperature and their absorbances are read at 532 nm against the blank. The inhibition induced by the precursor of B or $B_1$ or C=-$T_c$-Y—H in the confront of radical production by $Fe^{II}$ is determined by means of the following formula:

$$(1-A_s/A_c) \times 100$$

wherein $A_s$ and $A_c$ are respectively the absorbance values of the solution containing the tested compound+the iron salt and that of the solution containing only the iron salt, the compound meets test 5 when the inhibition percentage of radical production as above defined from the precursor of B or $B_1$ or C=-$T_c$-Y—H is higher than or equal to 50%.

Unexpectedly the invention products of the formulas (I) and (II) have an improved therapeutic index, in oxidative stress conditions, compared with the precursor drugs.

For illustrative purposes the above mentioned tests are referred to the following compounds (see the Examples):

Test 1: Precursor Drug: Indomethacin
  Maximum administrable dose to rats: 7.5 mg/Kg p.o. By administering a higher dose a toxicity is manifested, characterized by enteropathy, tremor, sedation until death (within 24 hours).
  The group of rats treated with NEM+indomethacin at the above mentioned dose shows gastrointestinal damages.
  Since indomethacin in the groups treated with NEM causes gastrointestinal damages, it meets test 1. indomethacin can therefore be used as a drug for preparing the compounds (I) and (II) of the present invention.

Test 2: Precursor Drugs: Indomethacin, Paracetamol and Mesalamine
  Indomethacin and paracetamol meet test 2 since the cellular damage (apoptosis) inhibition induced by CIP is not significantly different with respect to that of the controls.
  Therefore the above drugs can be used as drugs for preparing the compounds (I) and (II) of the present invention.
  On the contrary mesalamine does not meet test 2, since it inhibits the apoptosis induced by CIP. Therefore mesalamine according to test 2 could not be used as a precursor to prepare the compounds (I) and (II) of the present invention. It has been however found that mesalamine submitted to test 1 causes gastrointestinal damages.
  Thus also mesalamine can be used as a precursor for preparing the compounds (I) and (II) of the present invention.

Test 3 (L-NAME) Precurosr Drugs: Paracetamol, Simvastatin, Omeprazole
  Paracetamol and simvastatin meet test 3 since they cause gastric and hepatic damages greater than those induced both by L-NAME+carrier and by the drug+carrier.
  Therefore they can be used as precursors to prepare the compounds (I) and (II) of the present invention.
  On the contrary it has been found that omeprazole neither causes gastric nor hepatic damages, nor influences blood-pressure. According to test 3 omeprazole could not be used as a precursor for preparing the compounds (I) and (II) of the present invention.

Test 4 (Test for the Precursor of B and $B_1$): Precursor Compound: N-acetylcysteine and 4-thiazolidincarboxylic acid
  N-acetylcysteine in said test inhibits of 100% the production of radicals induced by DPPH. Since said percentage is higher than the limit of 50%, said drug cannot be used in the present invention as precursor of B or $B_1$.

4-Thiazolidincarboxylic acid does not inhibit at any extent the production of radicals induced by DPPH (Table V). Thus the drug does not meet test 4 as requested by the instant invention and it could be used as a precursor of B or $B_1$ if it meets test 5.

Test 5 (Test for the Precursor of B, $B_1$ and C=-$T_C$-Y—H): Precursor Compound: 4-thiazolidincarboxylic acid Table III relating to this test shows that the 4-thiazolidincarboxylic acid meets test 5 since the % inhibition is of 100%. Therefore the compound can be used as precursor of B or of $B_1$.

$Y^3$ in formula (III) is preferably selected from the following:

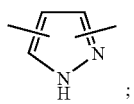 (Y1)

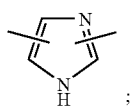 (Y2)

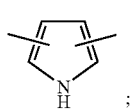 (Y3)

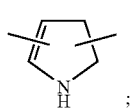 (Y4)

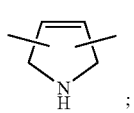 (Y5)

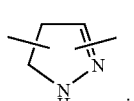 (Y6)

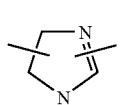 (Y7)

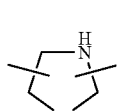 (Y8)

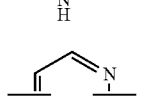 (Y9)

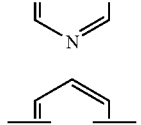 (Y10)

-continued

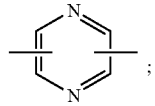 (Y11)

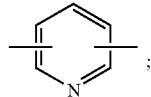 (Y12)

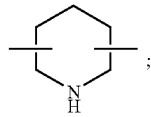 (Y13)

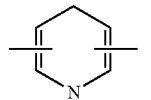 (Y14)

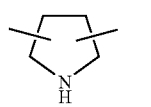 (Y15)

The most preferred of $Y^3$ is Y12 (pyridyl) substituted in positions 2 and 6. The bonds can also be in asymmetric position, for example Y12 (pyridyl) can be substituted also in position 2 and 3; Y1 (pyrazol) may be 3,5-disubstituted.

The compounds according to the present invention of formula (I) and (II) can be transformed into the corresponding salts. For example one way to form salts is the following: when in the molecule one nitrogen atom sufficiently basic to be salified, by reaction in organic solvent such as for example acetonitrile, tetrahydrofuran, is present, it is reacted with an equimolecular amount of the corresponding organic or inorganic acid. To form the salt, preferably in the formula of the invention compound Y or Y' of formula (III) is present.

Examples of organic acids are: oxalic, tartaric, maleic, succinic, citric acids.

Examples of inorganic acids are: nitric, hydrochloric, sulphuric, phosphoric acids.

The derivatives according to the invention can be used in the therapeutic indications of the precursor drug, allowing to obtain the advantages exemplified hereinafter for some groups of these drugs:

Anti-inflammatory drugs NSAIDs: the invention compounds result very well tolerated and effective, even when the organism is debilitated and is under conditions of oxidative stress. Said drugs can be used also in those pathologies wherein inflammation plays a significant pathogenetic role, such as for instance, but not limited to, in cancer, asthma, miocardic infarction.

Adrenergic blockers, of α- or β-blocker type: the action spectrum of the compounds of formula (I) results wider than that of the starting drugs: to a direct action on the smooth musculature the inhibition of the nervous beta-adrenergic signals governing the contraction of the hematic vessels is associated. The side effects (dyspnoea, bronchoconstriction) affecting the respiratory apparatus are lower.

Antithrombotic drugs: the antiplatelet activity is potentiated and in the case of the aspirin derivatives the gastric tolerability is improved.

Bronchodilators and drugs active on the cholinergic system: the side effects affecting the cardio-vascular apparatus (tachycardia, hypertension) result lowered.

Expectorants and mucolytic drugs: the gastrointestinal tolerability results improved.

Diphosphonates: the toxicity relating to the gastrointestinal tract is drastically lowered.

Phosphodiesterase (PDE) Inhibitors (bronchodilators): the therapeutic efficacy is improved, the dosage being equal; it is therefore possible, using the compounds of the invention to administer a lower dose of the drug and reduce the side effects.

Anti leukotrienic drugs: better efficacy.

ACE inhibitors: better therapeutic efficacy and lower side effects (dyspnoea, cough) affecting the respiratory apparatus.

Antidiabetic drugs (insulin-sensitizing and hypoglycaemizing), antibiotic, antiviral, antitumoral, anticolitic drugs, drugs for the dementia therapy: better efficacy and/or tolerability.

The drugs which can be used as precursors in the general formula of the compounds of the invention are all those meeting at least one of the above mentioned tests 1, 2, 3. Examples of precursor drugs which can be used are the following:

For anti-inflammatory/analgesic drugs, the following can for example be mentioned:

anti-inflammatory drugs: aceclofenac, acemetacin, acetylsalicylic acid, 5-amino-acetylsalicylic acid, alclofenac, alminoprofen, amfenac, bendazac, bermoprofen, α-bisabolol, bromfenac, bromosaligenin, bucloxic acid, butibufen, carprofen, cinmetacin, clidanac, clopirac, diclofenac sodium, diflunisal, ditazol, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glucametacin, glycol salicylate, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, naproxen, niflumic acid, oxaceprol, oxaprozin, oxyphenbutazone, parsalmide, perisoxal, phenyl acetylsalicylate, olsalazine, pyrazolac, piroxicam, pirprofen, pranoprofen, protizinic acid, salacetamide, salicilamide O-acetic acid, salicylsulphuric acid, salsalate, sulindac, suprofen, suxibuzone, tenoxicam, tiaprofenic acid, tiaramide, tinoridine, tolfenamic acid, tolmetin, tropesin, xenbucin, ximoprofen, zaltoprofen, zomepirac, tomoxiprol;

analgesic drugs: acetaminophen, acetaminosalol, aminochlorthenoxazin, acetylsalicylic 2-amino-4-picoline acid, acetylsalicylsalicylic acid, anileridine, benoxaprofen benzylmorphine, 5-bromosalicylic acetate acid, bucetin, buprenorphine, butorphanol, capsaicine, cinchophen, ciramadol, clometacin, clonixin, codeine, desomorphine, dezocine, dihydrocodeine, dihydromorphine, dimepheptanol, dipyrocetyl, eptazocine, ethoxazene, ethylmorphine, eugenol, floctafenine, fosfosal, glafenine, hydrocodone, hydromorphone, hydroxypethidine, ibufenac, p-lactophenetide, levorphanol, meptazinol, metazocine, metopon, morphine, nalbuphine, nicomorphine, norlevorphanol, normorphine, oxycodone, oxymorphone, pentazocine, phenazocine, phenocoll, phenoperidine, phenylbutazone, phenylsalicylate, phenylramidol, salicin, salicylamide, tiorphan, tramadol, diacerein, actarit.

For respiratory and urogenital apparatus drugs (bronchodilators and drugs active on the cholinergic system, expectorants/mucolytics, antiasthmatic/antiallergic antihistaminic drugs), the following can be mentioned: broncodilators and drugs active on the cholinergic system: acefylline, albuterol, bambuterol, bamifylline, bevonium methyl sulphate, bitolterol, carbuterol, clenbuterol, chlorprenaline, dioxethedrine, difylline, ephedrine, epinephrine, eprozinol, etafredine, ethylnorepinephrine, etofylline, fenoterol, flutoprium, bromide, hexoprenaline, ipratropium bromide, isoetharine, isoproteenerol, mabuterol, metaproterenol, oxybutynin, oxitropium bromide, pirbuterol, procaterol, protokylol, proxyphylline, reproterol, rimiterol, salmeterol, soterenol, terbutaline, 1-teobromineacetic acid, tiotropium bromide, tretoquinol, tulobuterol, zaprinast, cyclodrine, NS-21, 2-hydroxy-2,2-diphenyl-N-(1,2,3,6-tetra hydro-pyridin-4-ylmethyl)acetamide;

expectorant/mucolytic drugs: ambroxol, bromhexine, domiodol, erdosteine, guaiacol, guaifenesin, iodinated glycerol, letosteine, mesna, sobrerol, stepronin, terpin, tiopronin;

antiasthmatic/antiallergic antihistaminic drugs: acrivastine, alloclamide, amlexanox, cetirizine, clobenzepam, chromoglycate, chromolyn, epinastine, fexofenadine, formoterol, histamine, hydroxyzine, levocabastine, lodoxamide, mabuterol, metron s, montelukast, nedocromil, repirinast, seratrodast, suplatast tosylate, terfenadine, tiaramide, urushiol, bromhexine.

For cardiovascular drugs (ACE-inhibitors, beta-blockers, antithrombotic and vasodilator drugs, antidiabetic and hypoglycemic drugs), the following can be mentioned:

ACE-inhibitors: alacepril, benazepril, captopril, ceronapril, cilazapril; delapril, enalapril, enalaprilat, fosinopril, imidapril, lisinopril, losartan, moveltipril, naphthopidil, perindopril, quinapril, ramipril, spirapril, temocapril, trandolaoril, urapidil;

beta-blockers: acebutolol, alprenolol, amosulalol, arotinolol, atenolol, betaxolol, bevantolol, bucumolol, bufetolol, bufuralol, bunitrolol, bupranolol, butofilol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nebivolol, nifenalol, nipridalol, oxprenolol, penbutolol, pindolol, practolol, pronethalol, propranolol, sotalol, sulfinalol, talinolol, tertatolol, tilisolol, timolol, toliprolol, xibenolol;

antithrombotics and vasodilators: acetorphan, acetylsalicylic acid, argatroban, bamethan, benfurodil hemisuccinate, benziodarone, betahistine, brovincamine, bufeniode, citicoline, clobenfurol, clopidogrel, cyclandelate, dalteparin, dipyridamol, droprenilamine, enoxaoarin, fendiline, ifenprodil, iloprost, indobufen, isbogrel, isoxsuprine, heparin, lamifiban, midrodine, nadroparin, nicotinoyl alcohol, nylidrin, ozagrel, perhexiline, phenylpropanolamine, prenylamine, papaveroline, reviparin sodium salt, ridogrel, suloctidil, tinofedrine, tinzaparin, triflusal, xanthinol niacinate;

antidiabetic drugs: acarbose, carbutamide, glibornuride glybuthiazol(e), miglitol, repaglinide, troglitazone, 1-butyl-3-metanyl-urea, tolrestat, nicotinamide.

For antitumoral drugs, the following can be mentioned: ancitabine, anthramycin, azacitidine, azaserine, 6-azauridine, bicalutamide, carubicin, carzinophilin, chlorambucil, chlorozotocin, cytarabine, daunorubicin, defosfamide, demecolcine, denopterin, 6-diazo-5-oxo-L-norleucine, docetaxel, doxifluridine, doxorubicin, droloxifene, edatrexate, eflornithine, enocitabine, epirubicin, epitiostanol, etanidazole, etoposide, fenretinide, fludarabine, fluorouracil, gemcitabine, hexestrol, idarubicin, lonidamine, mannomustine, melphalan, menogaril, 6-mercaptopurine, methotrexate, mitobronitol, mitolactol, mitomycins, mitoxantrone, mopidamol, mycophenolic acid, ninopterin, nogalamycin, paclitaxel, pentostatin, pirarubicin, piritrexim, plicamycin, podophyllic acid, porfimer sodium, porfiromycin, propagermanium, puromycin, ranimustine, retinoic acid, roquinimex, streptonigrin, streptozocin, teniposide, tenuazonic acid, thiamiprine, thioguanine, tomudex, topotecan, trimetrexate, tubercidin, ubenimex, vinblastine, vincristine, vindesine, vinorelbine, zorubicin.

For antiulcer drugs the following can be mentioned: ϵ-acetamidocaproic acid, arbaprostil, cetraxate, cimetidine, ecabet, enprostil, esaprazole, irsogladine, misoprostol, omeprazole, ornoprostil, pantoprazole, plaunotol, rioprostil, rosaprostol, rotraxate, sofalcone, trimoprostil.

Among anti-hyperlipidemic drugs (statines) the following can be mentioned: atorvastatin, cilastatin, dermostatin, fluvastatin, lovastatin, mevastatin, nystatin, pentostatin, pepstatin, privastatin sodium, simvaszatin.

Among antibiotic/antiviral drugs the following can be mentioned:

antibiotics: amdinocillin, amoxicillin, ampicillin, apalcillin, apicycline, aspoxicillin, azidamfenicol, azidocillin, azlocillin, aztreonam, benzoylpas, benzyl penicillinic acid, biapenem, bicozamycin, capreomycin, carbenicillin, carindacillin, carumonam, cefaclor, cefadroxil, cefamandole, cefatrizine, cefazedone, cefazolin, cefbuperazone, cefclidin, cefdinir, cefditoren, cefepime, cefetamet, cefixime, cefinenoxime, cefmetazole, cefminox, cefodizime, cefonicid, cefoperazone, ceforanide, cefotaxime, cefotetan, cefotiam, cefoxitin, cefozopran, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, chloramphenicol, chlortetracycline, cinoxacin, clavulanic acid, clometocillin, cloxacillin, cyclacillin, cycloserine, demeclocycline, dicloxacillin, epicillin, fenbecillin, flomoxef, floxacillin, etacillin, imipenem, lenampicillin, loracarbef, lymecycline, mafenide, meclocycline, meropenem, metampicillin, methacycline, methicillin sodium, mezlocillin, minocycline, moxalactca, mupirocin, myxin, negamycin, novobiocin, oxacillin, panipenem, penicillin G potassium salt, penicillin N, penicillin O, penicillin V, phenethicillin potassium salt, pipacycline, piperacillin, pirlimycin, porfiromycin, propicillin, quinracillin, ritipenem, rolitetracycline, sancycline, sedecenycin, spectinomycin, sulbactam, sulbenicillin, temocillin, tetracycline, ticarcillin, tigemonam, tubercidin, azithromycin, clarithromycin, dirthromycin, enviomycin, erythromycin, josamycin, midecamycin, miokamycin, oleandomycin, rifabutin, rifamide, rifamycin, rifaximin, rokitamycin, spiramycin, troleandromycin, viomycin, virginiamycin;

amikacin, apramycin, arbekacin, dibekacin, dihydrostreptomycin, fortimicins, gentamicin, micronomicin, neomycin, netilmicin, paromomycin, ribostamycin, sisomicin, spectinomycin, streptomicin, tobramycin, trospectomycin;

bacampicillin, cefcapene pivoxil cefpodoxime proxetil, panipenem, pivampicillin, pivcefalexin, sultamicillin, talampicillin;

carbomycin, clindamycin, lincomycin, mikamycin, rosaramicin, ciprofloxacin, clinafloxacin, difloxacin, enoxacin, enrofloxacin, fleroxacin, flumequine, grepafloxacin, lomefloxacin, nadifloxacin, nalidixic acid, norfloxacin, ofloxacin, pazufloxacin, pefloxacin, pipemidic acid, piromidic acid, rufloxacin, sparfloxacin, tosufloxacin, trovafloxacin, clomocycline, guamecycline, oxytetracycline, nifurpirinol, nifurprazine; p-aminosalicylic acid, p-aminosalicylic acid hydrazide, clofazimine, deoxydihydrostreptomycin, ethambutol, glyconiazid, isoniazid, opiniazide, phenyl aminosalicylate, rifampin, rifapentine, salinazid, 4-4'-sulfynyldianiline, Acediasulfone, dapsone, succisulfone, p-sulfanilylbenzylamine, thiazolsulfone, acetyl sulfamethoxypyrazine, mafenide, 4'-(methylsulfamoyl)sulfanilanilide, salazosulfadimidine, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfamerazine, sulfameter, sulfamethazine, sulfamethizole, sulfamethomidine, sulfamethoxazole, sulfamethoxypyridazine, sulfamethylthiazole, sulfametrole, sulfamidochrysoidine, sulfamoxole, sulfanilamide, 2-p-sulfanilylanilinoethanol, $N^4$-sulfanilylsulfanilamide, sulfanilylurea, N-sulfanilyl-3,4-xylamide, sulfaperine, sulfaphenazole, sulfaproxyline, sulfapyrazine, sulfapyridine, sulfasomizole, sulfasymazine, sulfathiazole, sulfathiourea, sulfisomidine, sulfisoxazole, 4-sulfanilamido salicylic acid; negamycin, carumonan, cloxyquin, nitroxoline, arginine, metronidazole;

antiviral drugs: acyclovir, amantadine, cidofovir, cytarabine, didanosine, dideoxyadenosine, edoxudine, famciclovir, floxuridine, ganciclovir, idoxuridine, indanavir, kethoxal, lamivudine, MADU, penciclovir, podophyllotoxin, ribavirin, rimantadine, saquinavir, sorivudine, stavudine, trifluridine, valacyclovir, vidarabine, xenazoic acid, zalcitabine, zidovudine.

Among bone resorption inhibitors (diphosphonates) the following can be mentioned: alendronic acid, butedronic acid, etidronic acid, oxidronic acid, pamidronic acid, risedronic acid.

Among antidemence drugs the following can be mentioned: amiridine, lazabemide, mofegiline, salbeluzol, oxiracetam, ipidacrine, nebracetam, tacrine, velnacrine.

The preferred substances are the following:

among anti-inflammatory drugs: acetylsalicylic acid, 5-aminoacetylsalicylic acid, carprofen, diclofenac sodium, diflunisal, etodolac, flufenamic acid, flunixin, flurbiprofen, ibuprofen, indomethacin, indoprofen, ketoprofen, ketorolac, lornoxicam, loxoprofen, meclofenamic acid, mefenamic acid, meloxicam, mesalamine, naproxen, niflumic acid, olsalazine, piroxicam, salsalate, sulindac, suprofen, tenoxicam, tiaprofenic acid, tolfenamic acid, tolmetin, zomepirac, tomoxiprol;

among analgesic drugs: acetaminophen, acetylsalicylsalicylic acid, benoxaprofen, buprenorphine, butorphanol, capsaicin, diacereine, dihydrocodeine, ethylmorphine, eugenol, phenylbutazone, meptazinol, morphine, nalbuphine, pentazocine, thiorphan, tramadol, actarit.

Among respiratory and urogenital apparatus drugs: (bronchodilators, drugs active on the cholinergic system, expectorants/mucolytics, antiasthmatics/antiallergic antihistaminic drugs):

bronchodilators and drugs active on the cholinergic system: albuterol, carbuterol, clenbuterol, difylline, etofylline, fenoterol, ipratropium bromide, metaproterenol, oxybutynin, pirbuterol, salmeterol, terbutaline, tiotropium bromide, zaprinast, cyclodrine, NS-21, 2-hydroxy-2,2-diphenyl-N-(1,2,3,6-tetrahydro-pyridin-4-ylmethyl)acetamide;

expectorant/mucolytic drugs: ambroxol, bromexine, guaiacol, sobrerol;

antiasthmatic/antiallergic antihistaminic drugs: cetirizine, chromoglycate, histamine, levocabastine, lodoxamide, montelukast, terfenadine, bromexine.

Among cardiovascular drugs:

ACE-inhibitors: captopril, enalapril, lisinopril, losartan, ramipril;

beta blockers: alprenolol, atenolol, bupranolol, labetalol, metipranolol, metoprolol, pindolol, propranolol, timolol;

antithrombotic and vasoactive drugs: acetylsalicylic acid, acetorphan, argatroban, clopidogrel, dalteparin, dipyridamole, enoxaparin, heparin, iloprost, midodrine, ozagrel, phenylpropanolamine, trifusal;
antidiabetic drugs: tolrestat, nicotinamide.
Among antitumoral drugs: anthramycin, daunorubicin, doxorubicin, epirubicin, fluorouracil, methotrexate, vinblastine.
Among antiulcer drugs: cimetidine, omeprazole, pantoprazole.
Among antihyperlipidemic drugs: lovastatin, pravastatin sodium, simvastatin.
Among antibiotic/antiviral drugs:
antibiotic drugs: amoxicillin, ampicillin, aztreonam, biapenem, carbenecillin, cefaclor, cefadroxil, cefamandole, cefatrizine, cefoxitin, clavulanic acid, dicloxacillin, imipenem, meclocycline, methacycline, moxalactam, panipenem, sulbactam, azithromycin, erythromycin, josamycin, miokamycin, rifabutine, rifamide, rifamycin, gentamicin, paromomycin, sisomicin, bacampicillin, carbomycin, clindamycin, ciprofloxacin, clinafloxacin, difloxacin, enrofloxacin, lomefloxacin, nadifloxacin, norfloxacin, ofloxacin, pipemidic acid,
apicycline, clomocycline, oxytetracycline, nifurpirinol, nifurprazine, isoniazid, rifampin, rifapentine, dapsone, thiazolsulfone, sulfamethoxazole, sulfamoxole, metronidazole, arginine;
antiviral drugs: acyclovir, famciclovir, ganciclovir, penciclovir, ribavirin, vidarabine, zidovudine.
Among bone resorption inhibitors: alendronic acid, etidronic acid, pamidronic acid.
Among antidementia drugs: oxiracetam, tacrine, velnacrine.

The above mentioned substances, A precursors, are prepared according to the methods known in the prior art. See for example in "The Merck Index, 12a Ed. (1996), herein incorporated by reference. When available, the corresponding isomers, comprising optical isomers, can be used.

Tomoxiprol is obtained according to the method describeid in EP 12,866.

The compounds of formula (I) or (II) are prepared with synthesis methods mentioned below.

The choice of the reactions for each method depends on the reactive groups present in the precursor drug molecule, in the precursor compound of B or $B_1$, which can be, as above mentioned, bivalent or monovalent, and in the precursor compound of C.

The reactions are carried out with methods well known in the prior art, which allow to obtain bonds among the precursor drug, the precursor drug of B or $B_1$ and the precursor compound of C as above defined.

When the reactive function of the precursor drug (for example —COOH, —OH) is engaged in a covalent bond, for example of ester, amide, ether type, said function can be restored with the methods well known in the prior art.

Some synthesis schemes for obtaining the compounds of the invention are reported hereinafter:

A) Synthesis of the Compounds of Formula (I).
1. Synthesis of the compound obtained by reaction between the precursor drug and the compound precursor of B.
1a. When the drug has general formula R—COOH and the functional group of the precursor compound of B which binds itself to the drug carboxylic function has the formula XZ, X being as above defined and Z=H, the reactions carried out depend on the nature of the second reactive group present in the precursor compound of B.
1a.1 When the second reactive group present in the precursor compound of B is a carboxylic group, the synthesis general scheme expects the initial formation of the halide of the R—COHal acid (Hal=Cl, Br) and the subsequent reaction with the HX group of the precursor compound of B:

RCOOH---→RCOHal+H—X—$X_2$—COOH---→R-$T_1$-$T_B$-$X_2$—COOH (IA.1)

$X_2$, $T_1$, $T_B$ being as above defined.

When in the two reaction compounds other functional groups COOH and/or HX are present, they must be protected before the reaction according to the methods known in the art; for example as described in the volume by Th. W. Greene: "Protective groups in organic synthesis", Harward University Press, 1980.

The RCOHal acylhalide is prepared according to the methods known in the prior art, for example by thionyl or oxalyl chloride, $P^{III}$ or $P^V$ halides in inert solvents under the reaction conditions, such as for example toluene, chloroform, DMF, etc.

Specifically, if the HX group of the precursor-compound of B is $NH_2$, or OH or SH, the precursor drug of formula R—COOH is first converted into the corresponding acyl halide RCOHal, as above mentioned, and then reacted with the HX group of the precursor compound of B in the presence of an organic base, such as triethylamine, pyridine, etc. using an inert solvent in the reaction conditions such as toluene, tetrahydrofuran, etc. at a temperature in the range 0° C.-25° C.

Alternatively to the previous synthesis, the precursor drug of formula R—COOH can be treated with an agent activating the carboxyl group selected from N,N'-carbonyldiimidazol (CDI), N-hydroxybenzotriazol and dicyclohexylcarbodiimide in solvent such as for example DMF, THF, chloroform etc. at a temperature in the range −5° C.-50° C. and the obtained compound let react in situ with the reactive function of the precursor compound of B for obtaining the compound of formula (IA.1).

1a.2 When the precursor compound of B contains two functional groups XZ, equal to or different from each other, X being as above defined and Z=H, the precursor drug having formula R—COOH is first treated with an agent activating the carboxyl group, as above described in 1a.1, and then with the precursor compound of 3, after having protected one of the two reactive HX groups, for example by reaction with acetyl or ter-butyloxycarbonyl, restoring the initial function at the synthesis end. The scheme is the following:

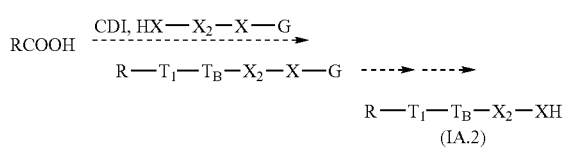

wherein X, $T_1$, $T_B$, $X_2$ are as above defined and G is a protective group of the HX function.

2. Nitroxyderivative synthesis.
2a.1 When the compound obtained at the end of the previous step 1a. has formula (IA.1), the acid can be converted into the corresponding sodic salt and then one can follow the known prior art methods for preparing the final compound, for example according to one of the following synthesis schemes:

A.)
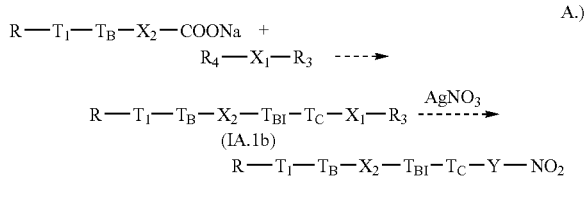

wherein $T_1$, $T_B$, $X_2$, $T_{BI}$, $T_C$ are as above defined, $R_4$ is selected from Cl, Br, Y is as above defined, $X_1$ is the Y radical free from the oxygen atom, $R_3$ is Cl, Br, Iodine, OH. When $R_3$=OH the compound of formula (1A.1b) is sbmitted to halogenation, for example with $PBr_3$, $PCl_5$, $SOCl_2$, $PPh_3+I_2$, and then reacted with $AgNO_3$ in organic solvent such as acetonitrile, tetrahydrofuran. If $R_3$ is Cl, Br, Iodine, the compound of formula (1A.1b) is directly reacted with $AgNO_3$ as above mentioned.

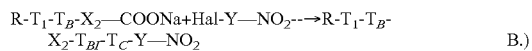
B.)

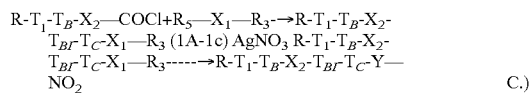
C.)

wherein $R_5$=OH or $NHR_{1C}$, $R_{1C}$, $R_3$ and the other symbols being as above defined.

The above shown reactions are well known in the prior art. See for example the patent applications in the name of the Applicant WO 94/12463, WO 95/09831 and WO 95/30641.

When $X_1$ is a linear $C_4$ alkyl, the corresponding acid $R-T_1-T_B-X_2$—COOH is reacted with triphenylphosphine in the presence of an halogenating agent such as $CBr_4$ or N-bromosuccinimide in tetrahydrofuran obtaining the compound (1A.1c) wherein $R_3$=Br.

2a.2 When the compound obtained at the end of the previous step 1a has formula (IA.2), the corresponding nitroxyderivative is obtained by treating an halogen-carboxylic acid of formula Hal-$X_1$—COOH, $X_1$ being as above defined, first with an agent activating the carboxyl group as described in 1A.1, and then with the compound of formula (IA.2), obtaining an halogen derivative, which is isolated and teen dissolved in organic solvent, (ref. paragraph 2a.1), and treated with silver nitrate. The global reaction scheme is the following:

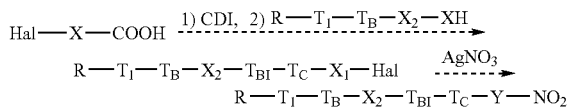

wherein $T_1$, $T_3$, $X_2$, $T_{BI}$, $T_C$, Y are as above defined.
Alternatively, the halide Hal-$X_1$—COCl can be used, wherein Hal is preferably bromine, which is reacted with the compound of formula (IA.2).

1b. When the drug precursor has the reactive function HX, wherein X is as above defined, instead of a carboxylic group, the two functional groups present on the precursor compound of B can be the following:

1b.1 A carboxylic group, which reacts with the HX function of the drug precursor, and a HX group, the latter reactive group of the precursor compound of B being equal to or different from the functional group of the drug precursor. The formula of the precursor compound of B is of the H—X—$X_2$—COOH type, wherein X and $X_2$ are as above defined. The H—X— function of the precursor compound of B is protected according to the known prior art methods and the carboxyl group is reacted, as above mentioned, according to the following scheme:

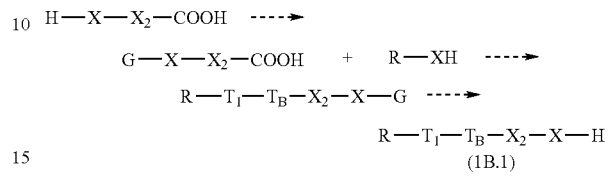

At the end of the reaction the HX function of the precursor compound of B is restored.

1b.2 When the precursor compound of B contains two carboxylic groups, it is treated with an equimolar amount of an agent activating the carboxyl group under the conditions previously described in 1a.1, and then reacted with the reactive HX function of the drug precursor molecule. Possible other reactive functions of HX type present in the two compounds must be protected as previously mentioned. Lastly a compound of formula $R-T_1-T_B-X_2$—COOH (1B.2) is obtained.

2b. Nitroxyderivative synthesis.

2b.1 To obtain the final nitroxyderivative starting from the compound of formula $R-T_1-T_B-X_2$—X—H (1B.1), obtained at the end of the synthesis described in 1b.1, the (1B.1) compound is reacted with an halogenacid of formula Hal-$X_1$—COOH which has been treated as previously described in paragraph 1a.1, or with the corresponding halogenacid chloride. The resulting compound is dissolved in organic solvent, for example acetonitrile or tetrahydrofuran and reacted with silver nitrate.

2b.2 To obtain the final nitroxyderivative starting from the compound of formula $R-T_1-T_B-X_2$—COOH (1B.2), obtained at the end of the synthesis described in 1b.2, the acid is transformed into the corresponding sodic salt, it is reacted with a $R_4$—$X_1$—$R_3$ compound, previously defined in the reaction A. scheme of paragraph 2a.1, obtaining according to the same process therein mentioned the final nitroxyderivative. Alternatively, when $X_1$ is a linear $C_4$ alkyl, the acid (1B.2) is reacted with triphenylphosphine in the presence of an halogenating agent such as $CBr_4$ or N-bromosuccinimide in tetrahydrofuran and the resulting compound dissolved in organic solvent for example acetonitrile, tetrahydrofuran, is reacted with silver nitrate.

2b.3 Alternatively to the synthesis process according to 1b.1 and 2b.1, it is possible to react in a first step the HX-function of the precursor compound of B HX—$X_2$—COOH with the acyl chloride of an halogenacid of formula Hal-$X_1$—CO—Cl, wherein Hal is preferably Br, and subsequently the carboxylic function of the so obtained compound, with the drug precursor R—HX. In the third and last step the -Hal group is substituted with —$ONO_2$ according to the process described in 2b.1. The reaction scheme is the following:

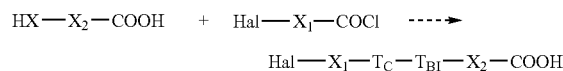

-continued

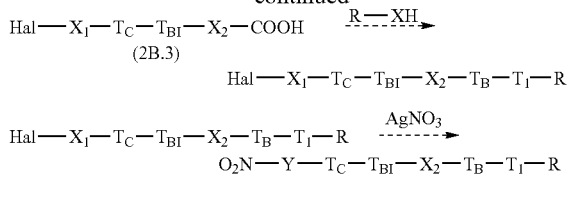

wherein $T_C$, $T_{BI}$, $T_B$, $T_1$, $X_2$, $X_1$, Y are as above defined. In the previous scheme the nitration can alternatively be carried out on the acid compound of formula (2B.3).

B) Synthesis of Compounds of Formula (II).

1a. When the drug precursor is of formula R—COOH and the precursor compound of $B_1$ contains only one functional reactive group of formula XH, X being as above defined, R—COOH is initially converted into the corresponding acylhalide, or treated with an agent activating the carboxyl group as described in 1a.1, and then reacted with the HX function of an halogen-acid compound, said function being equal to or different from that present on the precursor compound of $B_1$, said halogen-acid having the formula:

(IIA.1)

wherein $X_1'$ is $Y'$ as above defined without the oxygen atom through which the —NO$_2$ group is linked, X and Hal are as above defined.

The compound (IIA.1) can be obtained with the known method of the prior art. For example when X=NH, it can be obtained from the corresponding hydroxy-aminoacid, protecting the aminic group by the corresponding ter-butyloxycarbonyl derivative and transforming the hydroxyl function into halogen group as described for the halogenation of the compound (1A.1b) in 2a.1. The free carboxylic function of the compound resulting from the reaction with the molecule of the drug precursor is reacted with the function present in the molecule of the precursor compound of $B_1$, as previously illustrated in 1a.1 for the reaction between the R—COOH acid and the precursor compound of B. In the final step the halogen atom (Hal) present on the radical $X'_1$ is substituted with an ONO$_2$ group by adding AgNO$_3$ to an organic solution of the compound. The reaction scheme is the following, exemplified starting from the RCOCl acid halide:

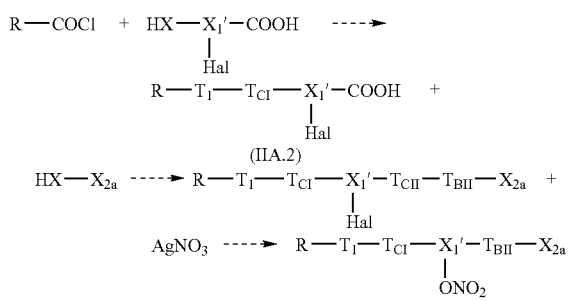

1b. When the drug precursor and the precursor compound of $B_1$ contain each a reactive group of general formula XH, the two groups in each of the two molecules being equal to or different from each other, wherein X is as above defined, the synthesis is carried out starting from an halogendiacid compound of formula

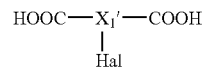

$X_1'$ being as above defined, said compound being prepared from the corresponding hydroxy-diacid as described for the halogenation of the compound (1A.1b) in 2a.1. The halogendiacid compound is treated with an equimolar amount of an agent activating the carboxyl group, under the conditions previously described in 1a.1., and then it is reacted with the reactive function of the drug precursor molecule. In the subsequent step the second carboxylic function is treated with an activating agent, as previously made for the first, and reacted with the precursor compound of $B_1$ according to the following scheme:

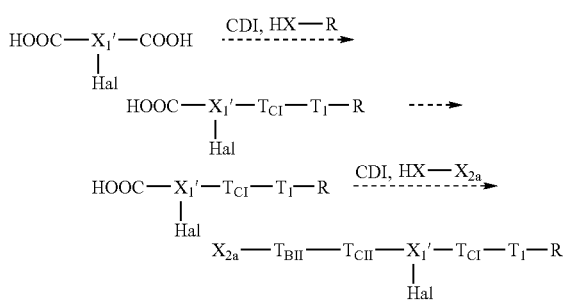

The halogen atom is then substituted with the ONO$_2$ group as above mentioned.

3. Synthesis of the nitroso (s=1) derivatives of formula (I).

3a.1 The compound of formula (1A.1b) wherein $R_3$=OH is reacted with sodium nitrite in a solvent formed of a mixture of water with tetrahydrofuran in the presence of hydrochloric acid. The reaction is widely illustrated in the prior art. The general scheme is the following:

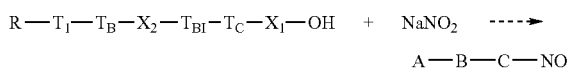

3a.2 WHen the compound obtained at the end of step A in 1a.2 has formula (IA.2) the corresponding nitroso derivative is obtained by treating an hydroxyacid of formula HO—$X_1$—COOH, $X_1$ being as above defined, first with an agent activating the carboxyl froup, as described in 1a.1, then reacting it with 1A.2 and the resulting product with sodium nitrite as described in 3a.1.

3b.1 To obtain the nitroso derivative starting from the compound of formula R-$T_1$-$T_B$-$X_2$—XH (1B.1) obtained at the end of the synthesis described in 1b.1, the compound (1B.1) is reacted with an hydroxyacid as described in 3a.2.

3b.2 To obtain the nitroso derivative from the compound of formula R-$T_1$-$T_B$-$X_2$—COOH (1B.2) obtained at the end of the synthesis described in 1b.2, the acid is transformed into the sodic salt and reacted with a compound Hal-$X_1$—OH, as previously described, and the obtained alcohol is treated as described in 3a.1.

4) Synthesis of the nitroso derivatives of formula (II)

4a.1 When the drug is of formula R—COOH and the precursor compound of $B_1$ contains only one function reactive group of formula XH, X being as above defined, R—COOH is initially converted into the corresponding acyl-halide or treated with an agent activating the carboxyl group as described in 1a.1, and then reacted with the HX function of an hydroxy-acid compound, said function being equal to or different from that present on the precursor compound of $B_1$, said hydroxy-acid having the formula:

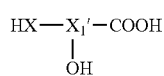
(4A.1)

wherein $X_1'$ is Y' as above defined without the oxygen atom through which the —NO group is linked, X is as above defined.

The free carboxylic function of the compound resulting from the reaction with the drug molecule is reacted with the function present in the molecule of the precursor compound of $B_1$, as previously illustrated in 1a.1 for the reaction between the R—COOH acid and the precursor compound of B. In the final step the alcohol is transformed into the nitroso-derivative as described in 3a.1.

The reaction scheme is the following, exemplified starting from the RCOCl acid halide:

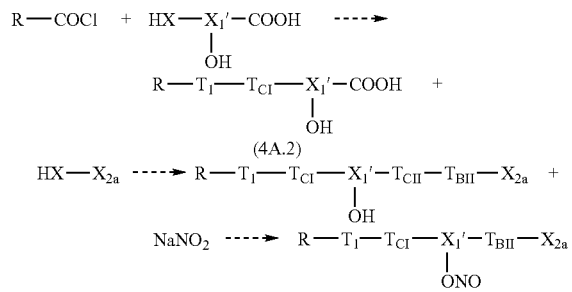

4b. When the drugs and the precursor compound of $B_1$ contain each a reactive group of general formula XH, the two groups in each of the two molecules being equal to or different from each other, wherein X is as above defined, the synthesis is carried out starting from an hydroxydiacid compound of formula

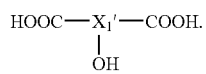

$X_1'$ being as above defined, said hydroxydiacid compound is treated with an equimolar amount of an agent activating the carboxyl group, under the conditions previously described in 1a.1., and then it reacted with the reactive function of the drug molecule. In the subsequent step the second carboxylic function is treated with an activating agent, as previously made for the first one, and reacted with the precursor compound of $B_1$ according to the following scheme:

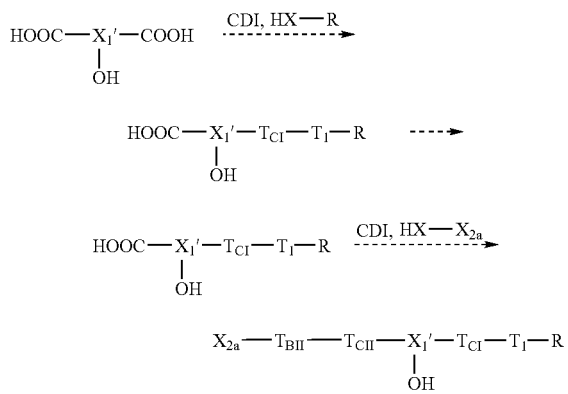

The obtained compound is reacted as described in 3a.1.

The compounds object of the present invention are formulated in the corresponding pharmaceutical compositions for parenteral, oral and topic use according to the well known methods in the art, together with the usual excipients; see for example the volume "Remington's Pharmaceutical Sciences 15a Ed."

The amount on molar basis of the active principle in these formulations is the same, or lower, in comparison with that used of the corresponding precursor drug.

The daily administrable doses are those of the precursor drugs, or optionally lower. The daily doses can be found in the publications of the field, such as for example in "Physician's Desk reference".

The following examples have the purpose to illustrate the invention and are not to be consioderaed as limitative of the same.

EXAMPLE 1

Synthesis of the 3-[2-fluoro-α-methyl-(1,1'-biphenyl)-4-acetyl]thiazolidin-4-carboxylic acid 4-(nitroxy)butyl ester (NO-Flurbiprofen), Compound NCX 2002

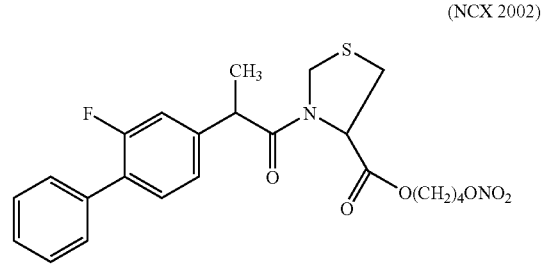

starting from flurbiprofen (formula IX) and the precursor of B is (L)-4-thiazolidin carboxylic acid (formula PIV)

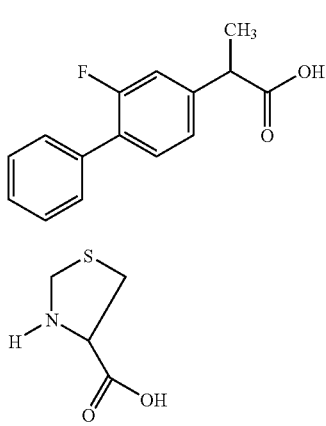

a) Synthesis of 3-[2-fluoro-α-methyl-(1,1'-biphenyl)-4-acetyl]thiazolidin-4-carboxylic acid To a solution of 2-fluoro-α-methyl-(1,1'-biphenyl)-4-acetic acid (10 g, 41 mmoles) in toluene (100 ml) and N,N-dimethylformamide (10 ml) cooled at 0° C., oxalylchloride (3.52 ml, 82 mmoles) is added. After 2 hours at room temperature, the solution is evaporated at reduced pressure. The obtained residue is dissolved in acetone (50 ml) and the solution is added to a solution of 4-thiazolidincarboxylic acid (5.44 g, 41 mmoles) and triethylamine (14.9 ml, 106 mmoles) in acetone (50 ml) cooled at 0° C. After 2 hours the solution is acidified with HCl 4 N, concentrated under vacuum, the residue is treated with ethyl acetate and the organic phase is washed first with HCl 2 N, then with water. The organic phase is anhydrified with sodium sulphate and evaporated at reduced pressure. By crystallization with ethyl acetate/n-hexane 9.4 g of the expected product in the form of a white solid having m.p. 142° C.-147° C., is obtained.

$^1$H-NMR (CDCl$_3$): 7.74-7.62 (4H, m), 7.35 (2H, t), 7.18-7.13 (2H, m), 5.06 (1H, m), 4.63 (1H, d), 4.42 (1H, d), 4.14 (1H, q), 3.13 (2H, m), 1.53 (3H, d).

b) Synthesis of the 3-[2-fluoro-α-methyl-(1,1'-biphenyl)-4-acetyl]thiazolidin-4-carboxylic acid 4-(bromobutyl) ester To a solution of the acid obtained in the previous step a) (9.43 g, 26.24 mmoles) in tetrahydrofuran (150 ml) triphenylhosphine (13.76 g, 52.49 mmoles) and carbon tetrabromide (17.4 g, 52.49 mmoles) are added. The reaction mixture is let under stirring for 24 hours at room temperature. The solvent is removed by evaporation at reduced pressure. The obtained crude product is purified by chromatography on silica gel eluting with n-hexane/ethyl acetate 8/2. 2.25 g of the ester are obtained in an oil form.

c) Synthesis of the 3-[2-fluoro-α-methyl-(1,1'-biphenyl)-4-acetyl]thiazolidin-4-carboxylic acid 4-(nitroxy)butyl ester To a solution of the ester obtained at the end of the previous step (2.6 g, 5.26 mmoles) in acetonitrile (20 ml) silver nitrate (1.07 g, 6.3 mmoles) is added. The reaction mixture is heated for 4 hours under reflux away from light. The formed salt is removed by filtration and the solution is evaporated at reduced pressure. The obtained residue is purified by chromatography or silica gel eluting with n-hexane/ethyl acetate 7/3. 0.84 g of the 3-[2-fluoro-α-methyl-(1,1'-biphenyl)-4-acetyl]thiazolidin-4-carboxylic acid 4-(nitroxy)butyl ester are obtained in an oil form.

$^1$H-NMR (CDCl$_3$): 7.56-7.09 (8H, m), 5.77 (1H, dd), 4.67 (2H, d), 4.51 (2H, t), 4.24 (2H, t), 4.15 (1H, q), 3.30-3.17 (2H, m), 1.74-1.70 (4H, m), 1.52 (3H, d).

EXAMPLE 2

Synthesis of the 3-(6-methoxy-α-methyl-2-naphthalenacetyl) thiazolidin-4-carboxylic acid 4-(nitroxy) butyl ester (NO-Naproxene) (NCX 2001)

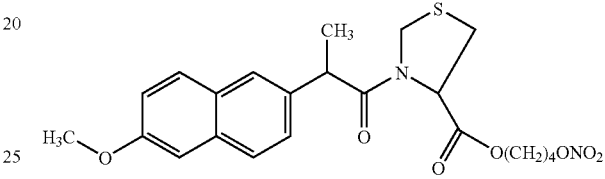

starting from naproxene (formula VI) and the precursor of B is (L)-4-thiazolidin carboxylic acid (formula PIV)

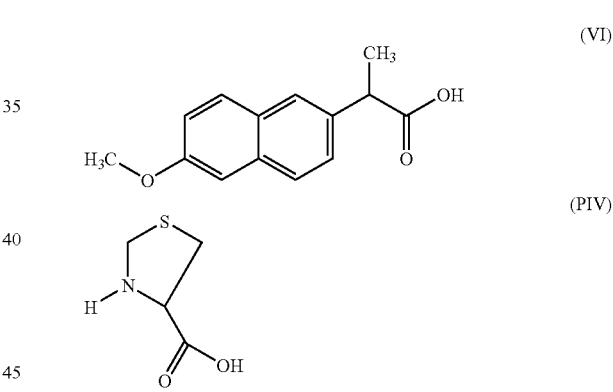

a) Synthesis of the 3-(6-methoxy-α-methyl-2-naphthalenacetyl) thiazolidin-4-carboxylic acid To a solution of 6-methoxy-α-methyl-2-naphthalenacetic acid (4.02 g, 17.5 mmoles) in toluene (30 ml) and N,N-dimethylformamide (0.3 ml) cooled at 0° C., oxalylchloride (2.92 ml, 34.06 mmoles) is added. After 2 hours at room temperature, the solution is evaporated at reduced pressure. The obtained residue is dissolved in acetone (50 ml) and the solution is added to a solution of 4-thiazolidincarboxylic acid (2.33 g, 17.5 mmoles) and triethylamine (6.34 ml, 45.5 mmoles) in acetone (50 ml) cooled at 0° C. After 2 hours the solution is acidified with HCl 4 N, concentrated under vacuum, the residue is treated with ethyl acetate and the organic phase is washed first with HCl 2 N, then with water. The organic phase is anhydrified with sodium sulphate and evaporated at reduced pressure. 4.43 g of the expected product are obtained in the form of a white solid having m.p. 165° C.-168° C.

¹H-NMR (CDCl₃): 7.75-7.66 (3H, m), 7.34 (1H, d), 7.14-7.11 (2H, m), 5.14 (1H, m), 4.80-4.61 (2H, m), 4.07 (1H, q), 3.91 (3H, s), 3.30-3.23 (2H, m), 1.53 (3H, d).

b) Synthesis of the 3-(6-methoxy-α-methyl-2-naphthalenacetyl) thiazolidin-4-carboxylic acid 4-(bromobutyl) ester To a solution of the acid obtained in the previous step a) (4 g, 11.6 mmoles) in tetrahydrofuran (50 ml) triphenylphosphine (6.07 g, 23.1 mmoles) and carbon tetrabromide (7.66 g, 23.2 mmoles) are added. The reaction mixture is left under stirring for 24 hours at room temperature. The solvent is removed by evaporation at reduced pressure. The obtained crude product is purified by chromatography on silica gel eluting with n-hexane/ethyl acetate 7/3. 2.25 g of the ester are obtained in an oil form.

c) Synthesis of the 3-(6-methoxy-α-methyl-2-naphthalenacetyl) thiazolidin-4-carboxylic acid 4-(nitroxy)butyl ester To a solution of the ester obtained at the end of the previous step (2 g, 4.16 mmoles) in acetonitrile (20 ml) silver nitrate (0.85 g, 5 mmoles) is added. The reaction mixture is heated for 5 hours under reflux away from light. The formed salt is removed by filtration and the solution is evaporated at reduced pressure. The obtained residue is purified by chromatography on silica gel eluting with n-hexane/ethyl acetate 7/3. 0.99 g of the 3-(6-methoxy-α-methyl-2-naphthalenacetyl)thiazolidin-4-carboxylic acid 4-(nitroxy)butyl ester are obtained in an oil form.

¹H-NMR (CDCl₃): 7.66 (3H, m), 7.38 (1H, m), 7.15 (2H, m), 5.06 (1H, dd), 4.66 (2H, d), 4.51 (2H, t), 4.25 (2H, t), 3.98 (1H, q), 3.92 (3H, s), 3.13 (2H, d), 1.84 (4H, m), 1.53 (3H, d).

EXAMPLE 3

Synthesis of the 3-(6-methoxy-α-methyl-2-naphthalenacetyl)-(R)-2-oxothiazolidin-4-carboxylic acid 4-(nitroxy) butyl ester (NCX 2150)

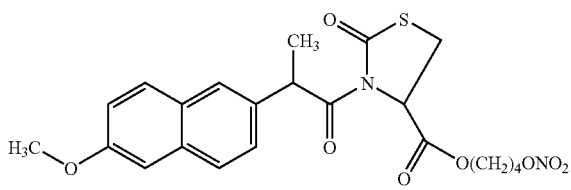

(NCX 2150)

starting from naproxene (formula VI) and the precursor of B is (L)-2-oxo-4-thiazolidin carboxylic acid (formula PV)

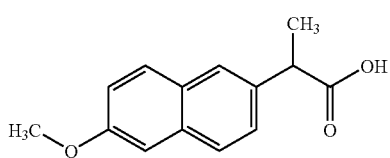

(VI)

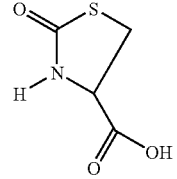

(PV)

a) Synthesis of the 3-(6-methoxy-α-methyl-2-naphthalenacetyl)(R)-2-oxothiazolidin-4-carboxylic acid To a solution of 6-methoxy-α-methyl-2-naphthalenacetic acid (7.0 g, 30.4 mmoles) in toluene (100 ml) and N,N-dimethylformamide (10 ml) cooled at 0° C., oxalylchloride (5.23 ml, 61 mmoles) is added. After 2 hours at room temperature the solution is evaporated at reduced pressure. To the solution of the obtained residue dissolved in tetrahydrofuran (50 ml) a mixture is added consisting of 2-oxothiazolidin-4-carboxylic acid (4.07 g, 27.6 mmoles), 4-dimethylaminopyridine (0.84 g, 6.9 mmoles), triethylamine (7.69 ml, 55.2 mmoles) in tetrahydrofuran (50 ml) cooled at −10° C. The mixture is left at room temperature for 24 hours. The reaction mixture is washed with HCl 5%, then with water. The organic phase is anhydrified with sodium sulphate and then evaporated at reduced pressure. The obtained residue is purified by chromatography on silica gel eluting with methylene chloride/methanol 95/5. 6.79 g of the expected product are obtained in the form of an amorphous solid.

b) Synthesis of the 3-(6-methoxy-α-methyl-2-naphthalenacetyl)-(R)-2-oxothiazolidin-4-carboxylic acid 4-(bromobutyl) ester To a solution of 3-(6-methoxy-α-methyl-2-naphthalenacetyl)-(R)-2-oxothiazolidin-4-carboxylic acid (6.79 g, 18.9 mmoles) in tetrahydrofuran (100 ml) triphenylphosphine (9.91 g, 37.8 mmoles) and carbon tetrabromide (12.53 g, 37.8 mmoles) are added. The reaction mixture is left under stirring for 16 hours at room temperature, then the solvent is removed by evaporation at reduced pressure. The obtained crude product is purified by chromatography on silica gel eluting with n-hexane/ethyl acetate 7/3. 1.83 g of the ester are obtained in the form of an oil.

c) Synthesis of the 3-(6-methoxy-α-methyl-2-naphthalenacetyl)(R)-2-oxothiazolidin-4-carboxylic acid 4-(nitrobutyl) ester To a solution of the ester obtained at the end of the previous step (1.7 g, 3.44 mmoles) in acetonitrile (20 ml) silver nitrate (0.82 g, 4.81 m=oles) is added. The reaction mixture is heated for 6 hours under reflux away from light. The formed salt is removed by filtration and the solution is evaporated under pressure. The obtained residue is purified by chromatography on silica gel eluting with n-hexane/ethyl acetate 7/3. 0.77 g of 3-(6-methoxy-α-methyl-2-naphthalenacetyl)-(R)-2-oxothiazolidin-4-carboxylic acid 4-(nitroxy)butyl ester are obtained in an oil form.

¹H-NMR (CDCl₃): 7.74-7.67 (3H, m), 7.47 (1H, m) 7.14-7.10 (2H, m), 5.28 (1H, dd), 4.12-3.51 (5H, m), 3.90 (3H, s), 3.63 (1H, dd), 3.33 (1H, dd), 1.55 (3×, d), 1.30-1.23 (4H, m).

EXAMPLE 4

Synthesis of [2-[(2,6-dichlorophenyl)amino]-benzeneacetyloxy]-(L)-histidine 4-(nitroxy)butyl ester

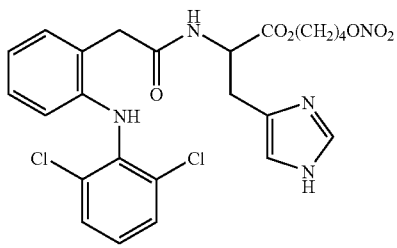

wherein the precursor drug of the invention compound is diclofenac of formula (XXIX) and the precursor compound of B is (L)-histidine of formula (PII):

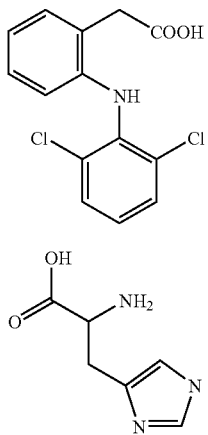

(XXIX)

(PII)

a) Synthesis of [2-[(2,6-dichlorophenyl)amino]benzeneacetyloxy] (L)-histidine To a diclofenac solution (3 g, 10.13 mmoles) in tetrahydrofuran (50 ml) cooled at 0° C., 1,1'-carbonyldiimidazol (1.69 g, 10.13 mmoles) is added under stirring. After 10 minutes the solution is treated with (L) histidine (1.57 g, 10.13 mmoles) and left under stirring at room temperature for 4 hours. The reaction mixture is concentrated under vacuum, treated with methylene chloride and then washed in sequence with HCl 1% and then with water. The organic phase is anhydrified with sodium sulphate and evaporated under vacuum. The obtained residue is purified by chromatography on silica gel column, eluting with ethyl acetate. [2-[(2,6-dichlorophenyl)amino] benzeneacetyloxy] (L)-histidine is obtained.

b) Synthesis of [2-[(2,6-dichlorophenyl)amino]benzeneacetyloxy] (L)-histidine 4-bromobutyl ester To a solution of [2-[(2,6-dichlorophenyl)amino]benzeneacetyloxy] (L)-histidine (5 g, 11.54 mmoles) in tetrahydrofuran (100 ml) triphenylphosphine (9.08 g, 34.62 mmoles) and carbon tetrabromide (11.48 g, 34.62 mmoles) are added under stirring. The reaction mixture is left at room temperature for 24 hours, then the solvent is removed by evaporation at reduced pressure. The obtained crude product is purified by chromatography on silica gel eluting with n-hexane/ethyl acetate 1/1. (S)-[2-[(2,6-dichlorophenyl)amino]benzeneacetyloxy] (L)-histidine 4-bromobutyl ester is obtained.

c) Synthesis of [2-[(2,6-dichlorophenyl)amino]benzeneacetyloxy] (L)-histidine 4-nitroxybutyl ester To a solution of [2-[(2,6-dichlorophenyl)amino]benzeneacetyloxy] (L)-histidine 4-bromobutyl ester (3 g, 5.28 mmoles) in acetonitrile (30 ml) silver nitrate (1.79 g, 10.56 mmoles) is added. The reaction mixture is heated under reflux for 6 hours sheltered from the light, the formed salt is removed by filtration and the solution is evaporated under reduced pressure. The obtained residue is purged by chromatography on silica gel column eluting with n-hexane/ethyl acetate 1/1. [2-[(2,6-dichlorophenyl)amino]benzeneacetyloxy] (L)-histidine 4-nitroxybutylester is obtained. Yield 35%.

EXAMPLE 5

Synthesis of 5-[[4-oxo-(4-nitroxybutyloxy)butanoyl]amino]-1,2,3,4-tetrahydroacridine

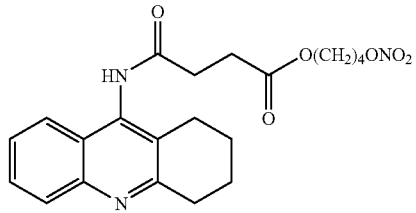

wherein the precursor drug of the invention compound is tacrine of formula (XXXV) and the precursor compound of the bridging group B is succinic acid of formula (RI):

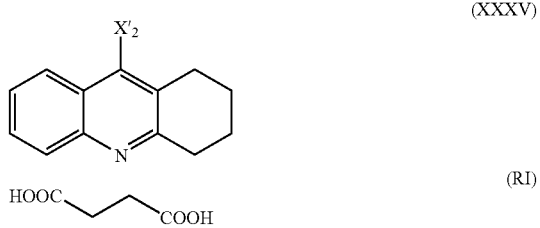

(XXXV)

(RI)

a) Synthesis of succinic acid 4-chlorobutyl monoester

To a solution of succinic anhydride (2 g, 19.98 mmoles) in chloroform (30 ml), cooled at 0° C., N,N'-dicyclohexylcarbodiimide (4.2 g, 20.35 mmoles) and 4-dimethylaminopyridine (100 mg, 0.8 mmoles) are added under stirring. After 30 minutes 4-chlorobutanol (2.1 g, 19.35 mmoles) is added. The reaction mixture is left at room temperature for 7 hours under stirring, then it is acidified with HCl 5% and it is extracted with ethyl acetate. The organic phase is washed with brine, anhydrified with sodium sulphate and evaporated at reduced pressure. The crude product is purified by chromatography on silica gel column eluting with methylene chloride/methanol 8/2. Succinic acid 4-chlorobutyl monoester is obtained.

b) Synthesis of 5-[[4-Oxo-(4-chlorobutyloxy)butanoyl]amino]-1,2,3,4-tetrahydroacridine To a solution of succinic acid 4-chlorobutyl monoester (2.9 g, 10.02 mmoles) in N,N-dimethylformamide (30 ml), cooled at 0° C., N,N'-dicyclohexylcarbodiimide (2.2 g, 10.66 mmoles) and 4-dimethylaminopyridine (100 mg, 0.8 mmoles) are added under stirring. After 5 minutes tacrine (2 g, 10.08 mmoles) is added. The reaction mixture is left at room temperature for 24 hours, then acidified with HCl 5% and extracted with ethyl acetate. The organic phase is washed with brine, anhydrified with sodium sulphate and evaporated at reduced pressure. The crude product is purified by chromatography on silica gel eluting with methylene chloride/methanol 8/2. 5-[[4-oxo-(4-chlorobutyloxy)-butanoyl]amino]-1,2,3,4-tetrahydroacridine is obtained.

c) Synthesis of 5-[[4-Oxo-(4-nitroxybutyloxy)butanoyl]amino]-1,2,3,4-tetrahydroacridine To a solution of 5-[4-oxo-[4-chlorobutyloxy)butanoyl]-amino]-1,2,3,4-tetrahydroacridine (3 g, 7,71 mmoles) in acetonitrile (50 ml) silver nitrate (1.79 g, 10.56 moles) is added under stirring. The reaction mixture is heated under reflux for 36 hours away from light, the formed salt is removed by filtration and the solution is evaporated at reduced pressure. The obtained residue is purified by chromatography on silica gel column eluting with ethyl acetate. 5-[[4-oxo-(4-nitroxybutyloxy)butanoyl]amino]-1,2,3,4-tetrahydroacridine is obtained. Yield 27%.

EXAMPLE 6

Synthesis of [4-amino-[4-oxo-(4-nitroxybutyloxy)butanoyl]-1-hyroxybutyliden] biphosphonic acid

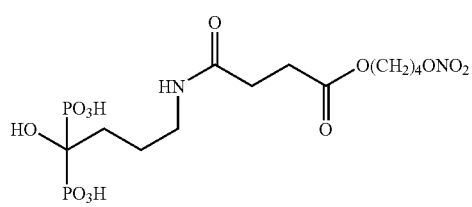

wherein the precursor drug of the invention compound is alendronic acid of formula (XXXVI) and the precursor compound of the bridging group B is succinic acid of formula (RI):

(XXXVI)

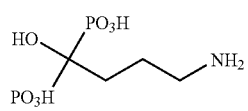

(RI)

HOOC⁀⁀COOH

The compound is synthetized following the synthesis procedure reported in Example 5. Yield 19%.

EXAMPLE 7

Synthesis of [4-oxo-(4-nitroxybutyloxy)butanoyl4-(2-amino-3,5-dibromophenyl)-methylamino] cyclohexanol ester

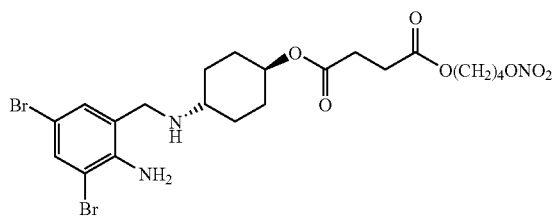

wherein the precursor drug of the invention compound is ambroxol of formula (XII) and the precursor compound of the bridging group B is succinic acid of formula (RI):

(XII)

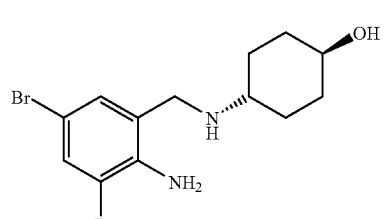

(RI)

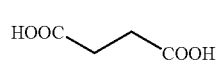
HOOC⁀⁀COOH a) Synthesis of 4-[(2-Tert-butoxycarbonylamino-3,5-dibromophenyl)methylamino] trans cyclohexanol To a mixture of 4-[(2-amino-3,5-dibromophenyl)methylamino]cyclohexanol (5 g, 13.22 mmoles) in dioxane (35 ml) and water (50 ml), triethylamine (3.31 ml, 23.7 mmoles) and di-tert-butyl dicarbonate (3.46 g, 15.86 moles) are added under stirring. After 24 hours the solution is concentrated under vacuum, treated with HCl 1% until having neutral pH in the solution, and it is extracted with ethyl acetate. The organic phase is anhydrified with sodium sulphate and evaporated under vacuum. 4-[(2-tert-butoxycarbonylamino-3,5-dibromophenyl) methyl amino]cyclohexanol is obtained which is used without further purification.

b) Synthesis of [4-Oxo-(4-chlorobutyloxy)butanoyl]-4-(2-tert-butoxycarbonylamino-3,5-dibromophenyl) methylamino] cyclohexanol ester To a solution of succinic acid 4-chlorobutyl monoester (4 g, 19.18 mmoli) in tetrahydrofuran (40 ml), 1,1'-carbonyldiimidazol (3.4 g, 20.96 mmoles) is added under stirring. After 10 minutes the solution is treated with 4-[(2-tert-butoxycarbonylamino-3,5-dibromophenyl) methyl amino]cyclohexanol (9.8 g, 20.5 mmoles) and it is left at room temperature for 4 hours. The reaction mixture is concentrated under vacuum, treated with methylene chloride, washed with HCl 1% and then with water. The organic phase is anhydrified with sodium sulphate and evaporated under vacuum. The obtained residue is purified by chromatography on silica gel column, eluting with n-hexane/ethyl acetate 1/1. [4-oxo-(4-chlorobutyloxy)butanoyl-4-(2-tert-butoxycarbonylamino-3,5-dibromophenyl) methylamino] cyclohexanol ester is obtained.

c) Synthesis of [4-Oxo-(4-nitroxybutyloxy)butanoyl-4-(2-tert-butoxycarbonylamino-3,5-dibromophenyl) methylamino] cyclohexanol ester To a solution of [4-oxo-(4-chlorobutyloxy)butanoyl-4-(2-tert-butoxycarbonylamino-3,5-dibromophenyl) methylamino] cyclohexanol ester (4 g, 5.98 mmoles) in acetonitrile (70 ml) silver nitrate (1.5 g, 8.83 mmoles) is added under stirring. The reaction mixture is heated under reflux for 24 hours away from light, the formed salt is removed by filtration and the solution is evaporated at reduced pressure. The obtained residue is purified by chromatography on silica gel eluting with n-hexane/ethyl acetate 7/3. [4-oxo-(4-nitroxybutyloxy)butanoyl-4-(2-tert-butoxycarbonylamino-3,5-dibromophenyl) methylamino] cyclohexanol ester is obtained.

d) synthesis of [4-[4-Oxo-(4-nitroxybutyloxy)butanoyl](2-amino-3,5-dibromo phenyl) methylamino] cyclohexanol ester To a solution of [4-oxo-(4-nitroxybutyloxy)butanoyl-4-(2-tert-butoxycarbonylamino-3,5-dibromophenyl) methylamino] cyclohexanol ester (3.2 g, 4.6 mmoles) in ethyl acetate (50 ml), cooled at 0° C., ethyl acetate/HCl 5N (6.5 ml) is added under stirring. The solution is left at 0° C. for 4 hours, the precipitate is filtered. The obtained crude product is treated with ethyl acetate and with 5% sodium bicarbonate, then with water. The organic phase is anhydrified with sodium sulphate and evaporated at reduced pressure. [4-oxo-(4-nitroxybutyloxy)butanoyl-4-(2-amino-3,5-dibromo phenyl) methylamino] cyclohexanol ester is obtained. Yield 17%.

PHARMACOLOGICAL TESTS

EXAMPLE

Acute Toxicity

Acute toxicity has been evaluated by administering to a group of 10 rats weighing 20 g a single dose of each of the tested compounds, by cannula, by os in an aqueous suspension of carboxymethylcellulose 2% w/v.

The animals are kept under observation for 14 days. In no animal of the group toxic symptoms appeared even after administration of a 100 mg/Kg dose.

EXAMPLE F1

Test 1—Experimental Model in Vivo with N-ethylmaleimide (NEM): Study of the Gastric Tolerability of Some Drugs Screened as Precursors of the Compounds of the Invention.

The animals (rats, weight about 200 g) are distributed in the following groups (No. 10 animals for group):

A) Control Groups:
1° group: treatment: only carrier (aqueous suspension 1% w/v of carboxymethylcellulose, dose: 5 ml/Kg when the drug is administered by os, physiologic solution when by parenteral route),
2° group: treatment: carrier+NEM B) Groups Administered with Each Drug:
group I: treatment: carrier+drug,
group II: treatment: carrier+drug+NEM.

The drugs assayed in this experiment are the following (Table I): indomethacin, ambroxol, mesalamine, sodic alendronate, tacrine, omeprazol, misoprostol.

Indomethacin, ambroxol and alendronate are administered by os, mesalamine by intracolonic (rectal) route and tacrine, omeprazol, misoprostol by subcutaneous route.

The maximum tolerated dose, determined by administering each substance by the above said routes to the animals not treated with NEM, is reported in Table I. With higher doses than those reported in the Table, enteropathy, diarrhoea, depression, tremor and sedation have appeared in the animals.

In this experimental model the animals are at first treated with NEM by subcutaneous injection at a dose of 25 mg/kg in physiologic solution. The drug is administered one hour later, in suspension in the carrier. Animals are sacrificed after 24 hours and evaluation of the damage to the gastrointestinal mucosa is made by counting the number of rats, inside each group, with lesions to the stomach at a visual inspection. The total number of said rats is then divided by the total number of rats of the group and multiplied by 100. The thus obtained percentages are reported in Table I. The Table shows that in the groups of rats treated with said drugs without NEM, no gastric lesions were detectable.

All the rats of group II (treated with NEM) showed gastric lesions after administration with the following drugs: indomethacin, ambroxol, mesalamine, sodic alendronate, tacrine. Said drugs therefore can be used in the synthesis of the products of the invention.

Omeprazol and misoprostol cannot instead be used, on the basis of the results provided in test 1, for preparing the products of the invention.

EXAMPLE F2

Test 2 (in Vitro): Inhibition of Apoptosis (DNA Fragmentation) Induced in the Endothelial Cells by CIP in the Presence of Some Drugs Screened as Precursors of the Compounds of the Invention.

The following precursor drugs (Table II): indomethacin, paracetamol, clopidogrel, salbutamol, ambroxol, sodic alendronate, diphylline, cetirizine, enalapril, nicotinamide, ampicilline, aciclovir, mesalamine, tacrine, simvastine, omeprazol have been tested.

Human endothelial cells of the umbilical vein are prepared according to a standard method. Fresh umbilical veins are filled with a collagenase solution 0.1% by weight and incubated at 37° C. for 5 minutes.

Subsequently the veins are perfused with the medium M 199 (GIBCO, Grand Island, N.Y.) pH 7.4 with 0.1% (weight/volume) of collagenase, added with 10% of bovine fetus serum (10 mcg/ml), sodium heparin (50 mcg/ml), thimidine (2.4 mcg/ml), glutamine (230 mcg/ml), penicillin (100 UI/ml), streptomycin (100 mcg/ml) and streptomycin B (0.125 mcg/ml). The cells are collected from the perfusate by centrifugation at 800 rpm and harvested in culture flasks T-75, pretreated with human fibronectin. Cells are then harvested in the same medium, added with bovine hypothalamic growth factor (100 ng/ml). When the cells of the primary cell culture (the cells directly removed from ex-vivo umbilical vein) form a single layer of confluent cells (about 8,000,000 cells/flask), harvesting is stopped and the layers are washed and trypsinized. The cellular suspensions are transferred into wells of a culture plate having 24 wells, half of said wells being added with the same culture medium containing the drug at a $10^{-4}$M concentration, and harvested in a thermostat at 37° C. at a constant moisture (90%), $CO_2$=5%. When the drug is not soluble in the culture medium, it is formerly dissolved in a small amount of dimethylsulphoxide. The maximum amount of dimethylsulphoxide which can be added to the culture medium is 0.5%. Only the cells coming from these first subcultures are used for the tests with cumene hydroperoxide (CIP). The cells are identified as endothelial cells by morphological examination and by the specific immunological reaction towards factor VIII; these cultures did never show contaminations from myocytes or fibroblasts.

Before starting the test, the cellular culture medium is removed and the cellular layers are carefully washed with a standard physiologic solution buffered with phosphate 0.1 M pH 7.0, at the temperature of 37° C. The content of each well is then incubated for one hour with a CIP suspension in the culture medium at a 5 mM concentration. Evaluation of the cellular damage (apoptosis) is carried out by determining the percent variation of the DNA fragmentation in the cultures containing the drug+CIP with respect to the controls treated with CIP only. Said % variation of DNA fragmentation is determined by evaluating the fluorescence variation by a BX60 Olympus microscope (Olympus Co., Roma) set at the wave length of 405-450 nm, of the test samples with respect to the optical density of the controls. The fluorescence of each sample was determined on 5 replicates. Statistic evaluation has been made with t Student test ($p<0.01$).

Results are given in Table II and show that indomethacin, paracetamol, clopidogrel, salbutamol, sodic alendronate, diphylline, cetirizine, enalapril, nicotinamide, ampicilline, aciclovir, tacrine, omeprazol do not significantly inhibit apoptosis; these drugs can therefore be used for preparing the products of the invention.

On the contrary ambroxol, mesalamine and simvastatine inhibit apoptosis. Therefore on the basis of the results of test 2 these compounds could not be used for preparing the products of the invention.

EXAMPLE F3

Test 3-Experimental in Vivo Model with $N^w$-nitro-L-arginine-methyl ester (L-NAME): Gastric Tolerability (Gastrointestinal Damage Incidence), Hepatic (GPT Dosage, Glutamic-pyruvic Transaminase) and Cardiovascular (Blood Pressure) Tolerability of Some Drugs Screened as Precursors of the Compounds of the Invention.

The experimental model adopted is according to J. Clin. Investigation 90, 278-281, 1992.

The endothelial dysfunction is evaluated by determining the damage induced by L-NAME administration to the gastrointestinal mucosa, the hepatic damage (GPT increase), and the vascular endothelium or cardiovascular damage as blood hypertension.

The animals (rats, average weight 200 g) are divided in groups as herein below described. The group receiving L-NAME is treated for 4 weeks with said compound dissolved at the concentration of 400 mg/litre in drinking water. The following groups (No. 10 animals for group) are constituted:

A) Control Groups:
1° group: treatment: only carrier (aqueous suspension 1% w/v of carboxymethylcellulose, dose: 5 ml/Kg when the drug is administered by os, physiologic solution when by parenteral route),
2° group: treatment: carrier+L-NAME, B) Groups Treated with the Drug:
3° group: treatment: carrier+drug,
4° group: treatment: carrier+drug+L-NAME.

The drugs used in the test are paracetamol, doxorubicin, simvastatine, omeprazol and misoprostol. Each drug is administered once a day for 4 weeks.

The maximum tolerated dose of the drug being administered to the animals is determined by evaluating, in a separate dose scaling up experiment on untreated animals, the appearance in the animals of symptoms such as enteropathy, diarrhoea, depression, tremor, sedation.

At the end of the four weeks access to water is prevented and after 24 hours the animals are sacrificed.

One hour before the sacrifice blood pressure is determined and a blood pressure increase is taken as an indication of a damage being occurred to vascular endothelium.

The damage to the gastric mucosa is evaluated as previously mentioned in test 1 (ex. F1). The hepatic damage is determined by evaluation after the sacrifice of the glutamic-pyruvic transaminase (GPT increase).

The drug meets, test 3 and it can therefore be used for preparing the compounds of the invention, when in the group of rats treated with L-NAME+drug+carrier, an higher hepatic damage (higher GPT values) and/or higher gastric damage and/or higher cardiovascular damage (higher blood pessure) are found in comparison with the group treated with the carrier only, or the group treated with carrier+drug, or the group treated with carrier+L-NAME.

The test results are reported in Table IV. The % gastric lesions have been determined as in Test 1. The % GPT and % blood pressure values are referred to the corresponding value found in the animals of the 1st group of the control groups. The average value of the blood pressure in this group was of 105±8 mmHg.

The results obtained show that paracetamol, doxorubicin and simvastatine cause hepatic damage and gastroenteropathy (GPT values and the gastric lesions are % higher compared both with the corresponding groups treated with the drug, in the absence of L-NAME, and with the controls treated with L-NAME).

These drugs can therefore be used for preparing the products of the invention.

Omeprazol and misoprostol should not instead be used, on the basis of this test, for preparing the products of the invention.

EXAMPLE F4

Test 4: Inhibition of the Radical Production from DPPH of Some Substances Used as Precursors of B or B1 (Ref. Formulas I and II of the Invention)

The method is based on a calorimetric test in which DPPH (2,2-diphenyl-1-picryl-hydrazyl) is used as the compound-forming radicals (M. S. Nenseter et Al., Atheroscler. Thromb. 15, 1338-1344, 1995).

Solutions in methanol of the tested substances at a final concentration 100 µM are initially prepared. 0.1 ml of each of these solutions are added to aliquots of 1 ml of a methanol solution 0.1 M of DPPH and then the final volume is brought to 1.5 ml. After having stored the solutions at room temperature away from light for 30 minutes, the absorbance at the wave length of 517 nm is read. It is determined the absorbance decrease with respect to the absorbance of a solution containing the same concentration of DPPH.

The efficacy of the test compound to inhibit the production of radicals, or antiradical activity, is expressed by the following formula:

$$(1-A_S/A_C) \times 100$$

wherein $A_S$ and $A_C$ are, respectively, the absorbance values of the solution containing the test compound together+DPPH and of the solution containing only DPPH.

The compound to be used according to the present invention does not meet test 4 if it inhibits radical production as above defined by a percentage of 50% or higher.

In Table V the results obtained with the following substances are reported: N-acetylcisteine, cisteine, ferulic acid, (L)-carnosine, gentisic acid, 4-thiazolidin carboxylic acid and 2-oxo-4-thiazolidincarboxylic acid.

Table V shows that:

- N-acetylcisteine, cisteine, ferulic acid, (L)-carnosine, gentisic acid meet test 4 since they inhibit the production of radicals induced by DPPH in an extent higher than 50%, therefore they cannot be used as precursors of B or $B_1$ of the compounds of the invention.
- 4-Thiazolidin carboxylic acid and 2-oxo-4-thiazolidincarboxylic acid do not meet test 4 since they do not inhibit radical production from DPPH in an extent equal or higher than 50%, and therefore they can be used as precursors of compounds B or $B_1$ according to the present invention, provided they meet following test 5.

EXAMPLE F5

Test 5: Inhibition of the Radical Production from $Fe^{II}$ from Compounds Used as Precursors of B, $B_1$ or $C=-T_C-Y-H$ 0.1 ml aliquots of $10^{-4}$ M methanolic solutions of 4-thiazolidin carboxylic acid and 2-oxo-4-thiazolidin carboxylic acid are added to test tubes containing an aqueous solution formed by mixing 0.2 ml of 2 mM deoxyribose, 0.4 ml of buffer phosphate pH 7.4 100 mM and 0.1 ml of 1 mM $Fe^{II}$ $(NH_4)_2(SO_4)_2$ in 2 mM HCl. The test tubes are then kept at a temperature of 37° C. for one hour. Then in each test tube are added in the order 0.5 ml of a 2.8% solution in trichloroacetic acid in water and 0.5 ml of an aqueous solution 0.1 M thio barbituric acid. A reference blank is constituted by substituting the above 0.1 ml aliquots of the test compound methanolic solutions with 0.1 ml of methanol. The test tubes are closed and heated in an oil bath at 100° C. for 15 minutes. A pink coloration develops the intensity of which is proportional to the quantity of deoxyribose undergone to radical oxidative degradation. The solutions are cooled at room temperature and their absorbances at 532 nm are read against the blank.

The inhibition induced by the precursor of B or $B_1$ or $C=-T_C-Y-H$ (wherein the free valence is saturated as above defined) in the confront of radical production from $Fe^{II}$ is determined as a percentage by means of the following formula:

$$(1-A_S/A_C) \times 100$$

wherein $A_S$ and $A_C$ are respectively the absorbance values of the solution containing the tested compound+the iron salt and that of the solution containing only the iron salt. The results are reported in Table III, from which it is drawn that both acids meet test 5, since they inhibit radical production from $Fe^{II}$ in a percentage higher than 50%. Therefore both 4-thiazolidin carboxylic acid and 2-oxo-4-thiazolidin carboxylic acid can be used as precursors of B, $B_1$ or of $C=-T_C-Y-H$, for obtaining the compounds of the present invention.

EXAMPLE F6

Gastric Tolerability Test of the Compounds According to the Invention in the Confront of the Corresponding Precursor Drugs in Conditions of Endothelial Dysfunctions Induced by L-NAME ($N^w$-nitro-L-arginine-methyl ester).

Example F3 was repeated and it was evaluated the gastric tolerability both of the following precursor drugs and of the corresponding derivatives according to the present invention:

- Diclofenac and the corresponding derivative according to Ex. 4.
- Ambroxol and the corresponding derivative according to Ex. 7.
- Alendronate and the corresponding derivative according to Ex. 6.
- Tacrine and corresponding derivative according to Ex. 5.

The results are reported in Table VI and show that, by administering at the same dose the compounds of the invention and the corresponding precursor drug, gastropathy incidence results remarkably reduced or disappeared in the groups treated with the compounds of the invention.

EXAMPLE 8

Synthesis of 3-[2-(acetyloxy)benzoyl]thiazolidin-4-carboxylic acid-4-(nitroxy)butyl ester (Formula XCI)

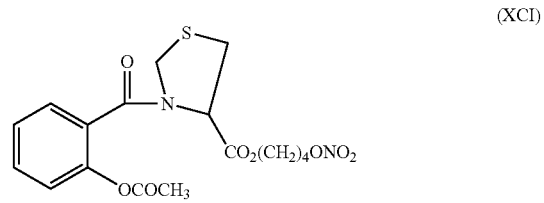

(XCI)

starting from acetylsalicylic acid (XCII) and thiazolidin-4-carboxylic acid (formula PIV)

(XCII)

(PIV)

Compound (XCI) is synthetized according to the scheme given in Example 7. Yield: 26%.

Elemental analysis

| calculated % | C 49.51 | H 4.89 | N 6.79 | S 7.77 |
|---|---|---|---|---|
| found % | C 49.57 | H 4.94 | N 6.70 | S 7.73 |

EXAMPLE 9

Synthesis of 2-(tert-butylamino)-1-[4-hydroxy-3[4-oxo-(4-nitroxybutyloxy)butiryloxy]methylphenyl] ethanol of formula (XCIII)

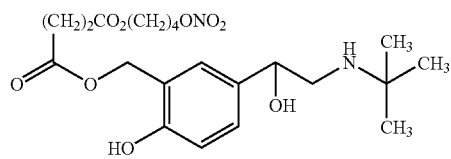
(XCIII)

starting from salbutamol (XXV) and succinic acid (formula RI).

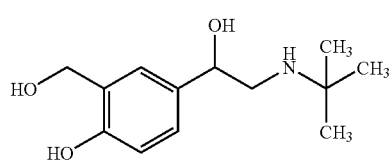
(XXV)

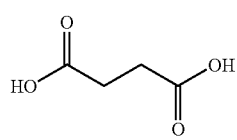
(RI)

Compound (XCIII) is obtained according to the procedure followed in Example 7. Yield: 14%.

Elemental analysis

| calculated % | C 55.26 | H 7.06 | N 6.14 |
|---|---|---|---|
| found % | C 55.20 | H 7.10 | N 6.17 |

EXAMPLE 10

Synthesis of 3-[[2-[4-[(4-chlorophenyl)phenylmethyl]-1-pyperazinyl]ethoxy]acetyl]-thiazolidin-4-carboxylic acid-4-(nitroxy)butyl ester of Formula (XCV)

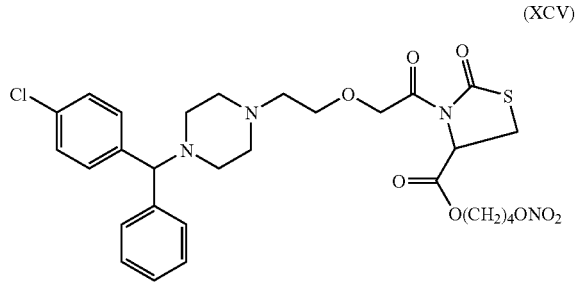
(XCV)

starting from cetirizine (XIV) and 2-oxo-4-thiazolidin carboxylic acid (formula PV)

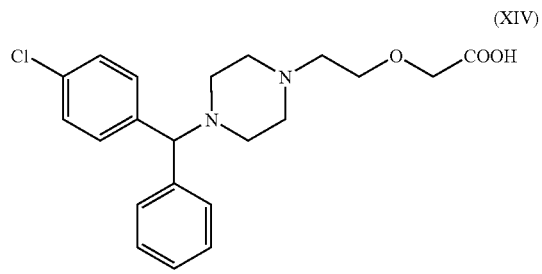
(XIV)

(PV)

Compound (XCIII) is obtained according to the procedure followed in Example 3. Yield: 18%.

Elemental analysis

| calculated % | C 55.44 | H 5.63 | N 7.66 | Cl 5.65 |
|---|---|---|---|---|
| found % | C 55.48 | H 5.60 | N 7.61 | Cl 6.71 |

EXAMPLE 11

Synthesis of N[(S)1-[N[1-(ethoxycarbonyl)-3-phenylpropyl]L-Alanyl]-L-prolinyl] hystidine 4(nitroxy) butyl ester of formula (XCVIII)

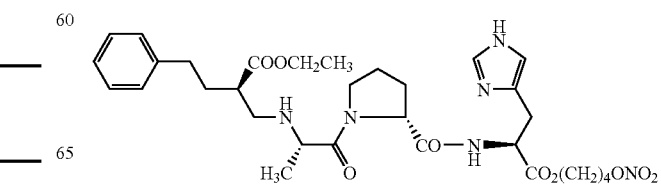
(XCVIII)

starting from enalapril of formula (XV) and histidine of formula (PII):

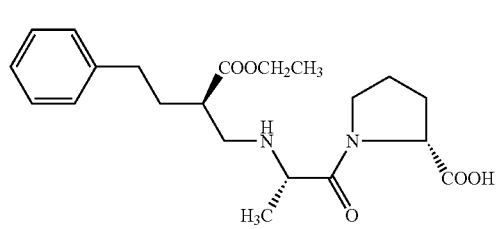
(XV)

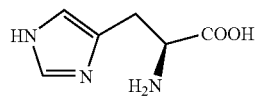
(PII)

Compound (XCVIII) is obtained according to the procedure of Example 7. Yield: 14%.
Elemental analysis

| calculated % | C 57.75 | H 6.88 | N 13.04 |
|---|---|---|---|
| found % | C 57.85 | H 6.95 | N 13.01 |

EXAMPLE 12

Synthesis of 1-[(1-methylethyl)-amino]-3-(1-naphtalenoxy)-2-[4-oxo-(4-nitroxybutyloxy)butanoyl]oxy propane of Formula (XCX)

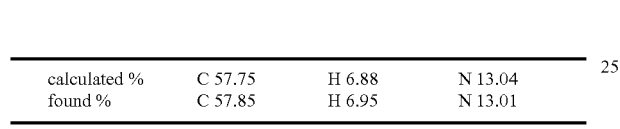
(XCX)

starting from propranolol of formula (XXIV) and succinic acid of formula (RI):

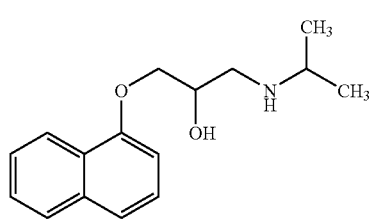
(XXIV)

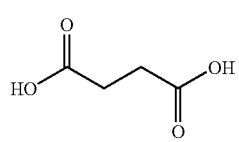
(RI)

Compound (XCX) is obtained according to the procedure of Example 7. Yield: 30%.
Elemental analysis

| calculated % | C 60.49 | H 6.77 | N 5.88 |
|---|---|---|---|
| found % | C 60.40 | H 6.75 | N 5.91 |

EXAMPLE 13

Synthesis of 3-[α-(2-chlorophenyl)-6,7-dihydro-thienol[3.2-c]pyridine-5(4H)acetyl]thiazolidin-4-carboxylic acid 4-(nitroxy)butyl ester of formula (XCXII)

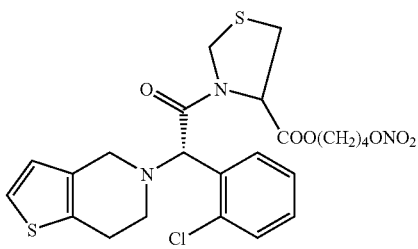
(XCXII)

starting from clopidogrel of formula (XI) and thiazolidin-4-carboxylic acid of formula (PIV):

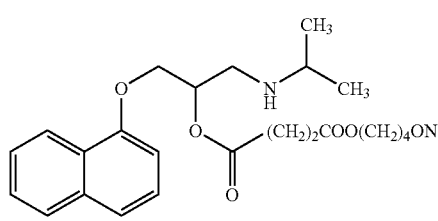
(XI)

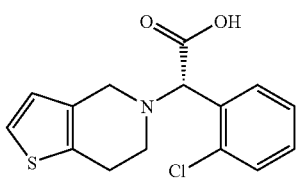
(PIV)

Compound (XCXII) is obtained according to the procedure followed in Example 1. Yield: 15%.
Elemental analysis

| calculated % | C 51.15 | H 4.85 | N 7.78 | S 11.87 | Cl 6.56 |
|---|---|---|---|---|---|
| found % | C 55.48 | H 5.60 | N 7.61 | S 11.85 | Cl 6.59 |

EXAMPLE 14

Synthesis of αN-[1-[5-(2,5-dihydro-5-oxo-3-furanyl)-3-methyl-2-benzofuranyl]ethyloxy-4-oxo-butanoyl] hystidine 4(nitroxy)butyl ester of Formula (XCXIV)

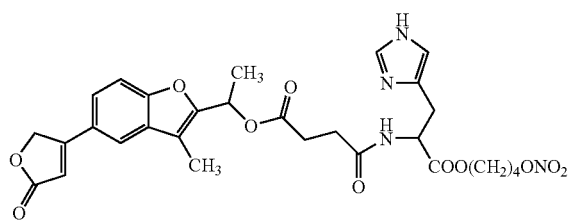
(XCXIV)

starting from benfurodil hemisuccinate of formula (XXXI) and hystidine of formula (PII)

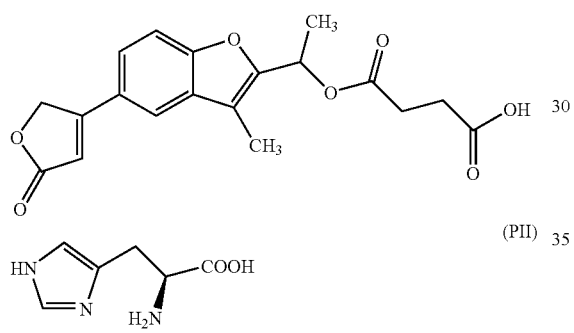
(XXXI)

(PII)

Compound (XCXIV) was obtained following the procedure described in Example 4. Yield: 35%.
Elemental analysis

| calculated % | C 56.86 | H 5.26 | N 9.15 |
| found % | C 56.92 | H 5.29 | N 9.10 |

EXAMPLE 15

Synthesis of 3-nicotinoyl-thiazolidin carboxylic acid (4-nitroxy)butyl ester of Formula (XCXVI)

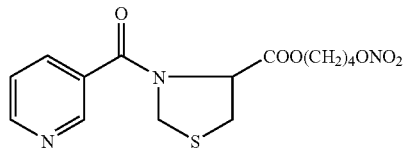
(XCXVI)

starting from nicotinamide of formula (XXIII) and thiazolidin-4-carboxylic acid of formula (PIV)

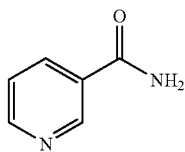
(XXIII)

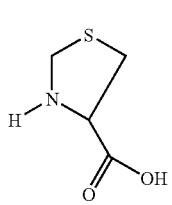
(PIV)

Compound (XXIII) was synthetized according to the procedure described in Example 1, using nicotinic acid. Yield 35%
Elemental analysis

| calculated % | C 47.32 | H 4.82 | N 11.82 | S 9.01 |
| found % | C 47.30 | H 4.79 | N 11.84 | S 9.06 |

EXAMPLE 16

Synthesis of 5-methoxy-2-[[[4-oxo-4-(nitroxy)butyryloxy]-3,5-dimethyl-2-pyridinyl]methyl]sulphinyl]-1H-benzimidazole of formula (XCXVIII)

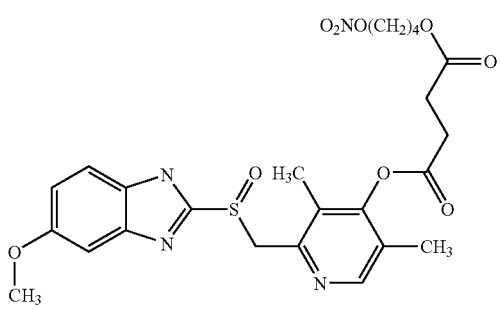
(XCXVIII)

starting from 4-hydroxyomeprazole of formula (XXII) and succinic acid of formula (RI)

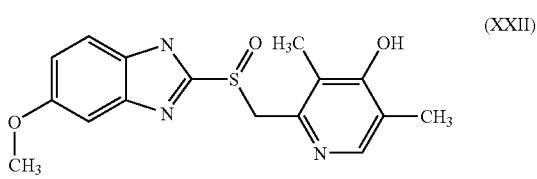
(XXII)

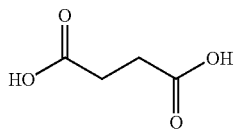
(RI)

Compound (XCXVIII) was obtained following the procedure described in Example 7. Yield 15%

Elemental analysis

| calculated % | C 52.64 | H 4.97 | N 10.23 | S 5.86 |
|---|---|---|---|---|
| found % | C 52.68 | H 5.01 | N 10.15 | S 5.81 |

EXAMPLE 17

Synthesis of [1S-[1α,3α,7β,8β,(2S*,4S*)]]-2,2-dimethylbutanoic acid 1,2,3,7,8,8-hexahydro-3,7-dimethyl-8-[2-[tetrahydro-4-[4-oxo-(4-nitroxybutyloxy)butiryloxy]-6-oxo-2H-piran-2-yl]ethyl]-1-naphthalenyl ester of Formula (XCXIX)

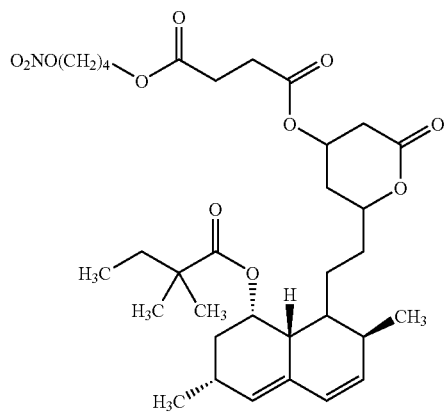
(XCXIX)

starting from simvastatine of formula (XXI) and succinic acid of formula (RI)

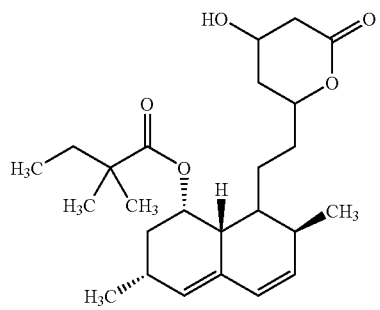
(XXI)

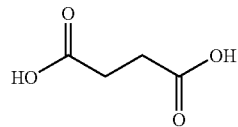
(RI)

Compound (XCXIX) was synthetized following the procedure of Example 7. Yield 12%.

Elemental analysis

| calculated % | C 62.35 | H 7.77 | N 2.20 |
|---|---|---|---|
| found % | C 62.50 | H 7.81 | N 2.17 |

EXAMPLE 18

Synthesis of 3-[4-D-α-aminobenzylpenicillaminoyl] thiazolidin carboxylic acid 4-(nitroxy)butyl ester of Formula (XCXX)

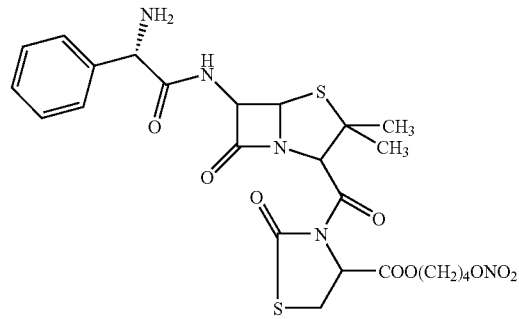
(XCXX)

starting from ampicillin of formula (XVI) and 2-oxo-4-thiazolidin carboxylic acid of Formula (PV)

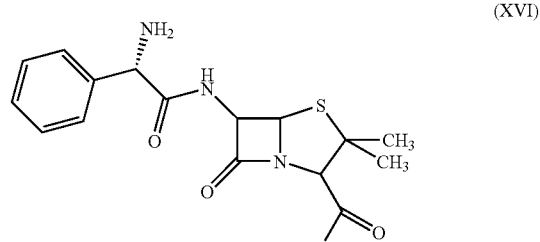
(XVI)

(PV)

Compound (XCXX) was obtained following the procedure of Example 3. Yield 19%.

Elemental analysis

| calculated % | C 48.39 | H 4.91 | N 11.76 | S 10.77 |
|---|---|---|---|---|
| found % | C 48.43 | H 4.99 | N 11.71 | S 10.74 |

EXAMPLE 19

Synthesis of 9-[[2-[4-oxo-(4-nitroxybutyloxy)butiryloxy]ethoxy]-methyl]guanine of Formula (XCXXI)

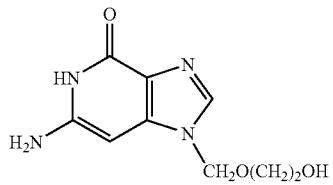
(XVII)

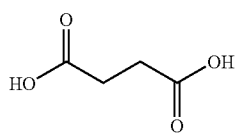
(RI)

Compound (XCXXI) was synthetized following the procedure of Example 7. Yield: 23%.

Elemental analysis

| calculated % | C 46.26 | H 5.25 | N 15.85 |
|---|---|---|---|
| found % | C 46.30 | H 5.28 | N 15.84 |

EXAMPLE 20

Synthesis of (8S-cis)-10[(3-amino,2,3,6-tri-deoxy-α-L-lyxo-exo pyranosyl)oxy]-7,8,9,10-tetrahydro,6,8,11-trihydroxy-8-[[[4-oxo-(4-nitroxybutyloxy)butiryloxy-]methyl-oxo]-1-methoxy-5,12-naphtiacenedione of Formula (XCXXII)

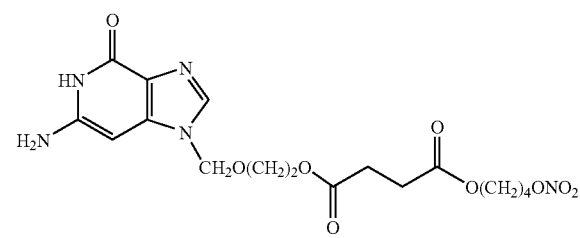
(XCXXI)

starting from acyclovir of formula (XVII) and succinic acid of Formula (RI)

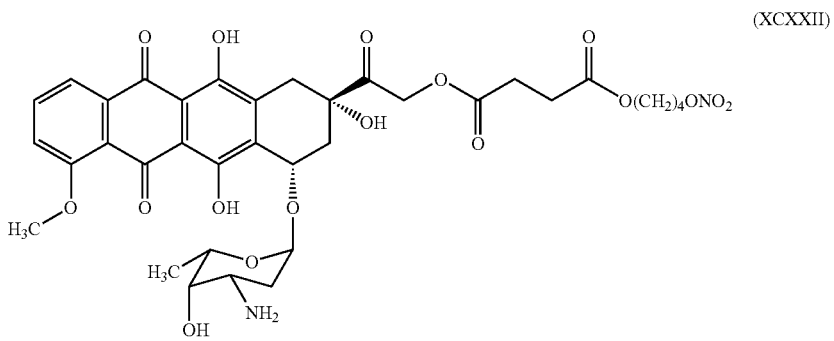
(XCXXII)

starting from doxorubicin of formula (XXXII) and succinic acid of formula (RI)

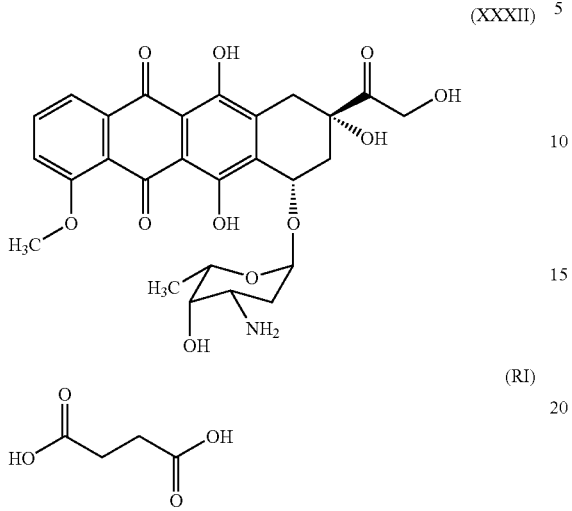

(XXXII)

(RI)

Compound (XCXXII) was synthesized according to the procedure of Example 7. Yield 10%.

Elemental analysis

| calculated % | C 55.26 | H 5.30 | N 3.68 |
|---|---|---|---|
| found % | C 55.34 | H 5.32 | N 3.65 |

EXAMPLE F7

Example F1 was repeated with four groups of rats (each group of of ten animals), all of them receiving NEM, and orally administered as it follows:

a. control group: the vehicle formed of an aqueous suspension 1% w/v of carboxymethylcellulose,
b. one group (group b—comparative) administered at the same time with 5 mg/Kg (0.02 mmoles/Kg) of flurbiprofen+2.7 mg/Kg (0.02 mmoles/Kg) of 4-thiazolidin carboxilic acid in the same above vehicle,
c. one group (group c—comparative) administered at the same time with 7.4 mg/Kg (0.02 mmoles/Kg) of 4-(nitroxy)butyl ester of flurbiprofen, synthetized according to the method described in WO 94/12463, +2.7 mg/Kg (0.02 mmoles/Kg) of 4-thiazolidin carboxilic in the same above vehicle,
d. one group (group d) administered with 9.8 mg/Kg (0.02 mmoles/Kg) of 3-[2-fluoro-α-methyl-(1,1'-biphenyl)-4-acetyl]thiazolidin-4-carboxylic acid 4-(nitroxy)butyl ester synthetized as from Ex. 1(indicated as NO-Flurbiprofen in Table VII), in the above same vehicle.

The results are reported in Table VII and show that the mixtures administered respectively to groups b and c (comparatives), differently from the compound of the invention administered to group d, were almost ineffective (group b) or much less effective (group c) in reducing gastric lesions.

TABLE I

Test 1: Gastric tolerability of drugs representative of the drug classes illustrated in the present invention in animals not treated or treated with NEM (oxidative stress conditions). The % is calculated from the ratio between the number of animals found with gastric lesions and that total of the group.

| Compound | dose (mg/Kg)/ admin. route | Gastro-enteropathy (% incidence) | |
|---|---|---|---|
| | | without NEM | with NEM |
| carrier | | 0 | 0 |
| Indomethacin | 7.5/p.o. | 0 | 100 |
| Ambroxol | 25/p.o. | 0 | 80 |
| Mesalamine | 750/i.c. | 0 | 60 |
| Alendronate | 15/p.o. | 0 | 90 |
| Tacrine | 1/s.c. | 0 | 100 |
| Omeprazol | 30/s.c. | 0 | 0 |
| Misoprostol | 0.5/s.c. | 0 | 0 | p.o. = per os;
i.c. = by intracolonic route;
s.c. = by subcutaneous route.

TABLE II

Test 2: Inhibition of apoptosis (DNA fragmentation) induced by CIP in the endothelial cells in the presence of compounds representative of the drug classes illustrated in the present invention.

| Compound | Apoptosis % with respect to the controls treated only with CIP |
|---|---|
| Indomethacin | 95 |
| Paracetamol | 120 |
| Clopidogrel | 110 |
| Salbutamol | 90 |
| Ambroxol | 70 |
| Alendronate | 160 |
| Diphylline | 95 |
| Cetirizine | 115 |
| Enalapril | 80 |
| Nicotinamide | 98 |
| Ampicilline | 94 |
| Aciclovir | 95 |
| Mesalamine | 74 |
| Tacrine | 90 |
| Simvastatine | 72 |
| Omeprazol | 90 |

TABLE III

Test 5: Screening of the effectiveness of the listed substances to inhibit radical production induced by $Fe^{II}$

| Compound | % Radical Inhibition from $Fe^{II}$ |
|---|---|
| Blank | 0 |
| 2-oxo-4-thiazolidin carboxylic acid | 100 |
| 4-thiazolidin carboxylic acid | 100 |
| histidine | 90 |
| succinic acid | 90 |

TABLE IV

Test 3: Gastric tolerability (gastrointestinal damage incidence), hepatic (GPT, glutamic-pyruvic transaminase dosage), and cardiovascular (blood pressure) of some compounds representative of the drug classes illustrated in the present invention under conditions of endothelial trouble induced by L-NAME.
The results relating to the blood pressure and GPT are expressed as % values compared with those found in animals treated with the only carrier, without L-NAME.

| Compound | dose mg/Kg/ administ. route | Blood pressure % without L-NAME | Blood pressure % with L-NAME | GPT % without L-NAME | GPT % with L-NAME | Gastroenteropathy % without L-NAME | Gastroenteropathy % with L-NAME |
|---|---|---|---|---|---|---|---|
| Carrier | | 100 | 152 | 100 | 155 | 0 | 30 |
| Paracetamol | 300/i.p. | 108 | 155 | 180 | 500 | 20 | 90 |
| Doxorubicin | 1/i.p. | 120 | 145 | 195 | 360 | 30 | 100 |
| Simvastatine | 50/p.o. | 85 | 148 | 122 | 220 | 0 | 60 |
| Omeprazol | 30/s.c. | 100 | 150 | 100 | 160 | 0 | 10 |
| Misoprostol | 0.5/s.c. | 100 | 142 | 100 | 160 | 0 | 5 |

TABLE V

Test 4: Screening of the effectiveness of the listed compounds in inhibiting radical production from DPPH.

| Compound | % inhibition radical production from DPPH |
|---|---|
| Solvent | 0 |
| N-acetylcisteine | 100 |
| Cisteine | 100 |
| Ferulic acid | 100 |
| (L)-carnosine | 80 |
| Gentisic acid | 80 |
| 2-oxo-4-thiazolidin carboxylic acid | 0 |
| 4-thiazolidin carboxylic acid | 0 |
| histidine | 0 |
| succinic acid | 0 |

TABLE VI

Study on gastric tolerability of the listed drugs and of the corresponding derivatives according to the invention on animals not treated or treated with L-NAME

| Compound | animals not treated with L-NAME dose mg/Kg | animals not treated with L-NAME % gastropathy | animals treated with L-NAME dose mg/Kg | animals treated with L-NAME % gastropathy |
|---|---|---|---|---|
| Carrier | — | 0 | — | 0 |
| Diclofenac (comp.) | 20/p.o. | 70 | 5/p.o. | 100 |
| Derivative Ex. 4 | 20/p.o. | 0 | 5/p.o. | 0 |
| Ambroxol (comp.) | 100 p.o. | 60 | 25 p.o. | 80 |
| Derivative Ex. 7 | 100 p.o. | 10 | 25 p.o. | 0 |
| Alendronate (comp.) | 100 p.o. | 90 | 15 p.o. | 70 |
| Derivative Ex. 6 | 100 p.o. | 20 | 15 p.o. | 10 |
| Tacrine (comp.) | 10/s.c. | 80 | 1/s.c. | 70 |
| Derivative Ex. 5 | 10/s.c. | 20 | 1/s.c. | 0 |

TABLE VII

Test on gastric tolerability following oral administration of NEM (ex. F7)

| groups | dose mg/Kg p.o. | Gastropathy % incidence |
|---|---|---|
| controls | — | — |
| group b - comparative mixture flurbiprofen (A) + 4-thiazolidin carboxylic acid (B) | 5(A) + 2.7(B) | 80 |
| group c - comparative mixture flurbiprofen 4-(nitroxy)butyl ester (C) + 4-thiazolidin carboxylic acid (B) | 7.4(C) + 2.7(B) | 20 |
| group d NO-Flurbiprofen (ex. 1) | 9.8 | 0 |

The invention claimed is:

1. Compounds or their salts having the following general formula (I):

A-B-$T_c$-Y—$NO_2$  (I)

wherein:

A=R-$T_1$-, wherein

R is the radical of a drug having formula R-$T_1$-H or R-$T_1$-OH selected from the group of cardiovascular drugs consisting of:

ACE-inhibitors: captopril, enalapril, lisinopril, losartan and ramipril;

beta blockers: alprenolol, atenolol, bupranolol, labetalol, metipranolol, metoprolol, pindolol, propanolol, timolol;

antithrombotic and vasoactive drugs: argatroban, clopidogrel, dipyridamole, iloprost, ozagrel, triflusal;

antidiabetic drugs: nicotinamide, tolrestat;

$T_1$=(CO) or X wherein:

X=O, S, N, $NR_{1C}$ wherein $R_{1C}$ is H or a linear or branched $C_1$-$C_5$ alkyl, B=-$T_B$-$X_2$-$T_{BI}$- wherein $T_B$ and $T_{BI}$ are equal or different, are $T_B$=(CO) when $T_1$ is X, $T_B$=X when $T_1$ is (CO), X being as above defined;

$T_{BI}$=(CO) or X, X being as above defined;

$X_2$ is a bivalent bridging group between $T_B$ and $T_{B1}$, wherein $-T_B-X_2-T_{B1}-$ is selected from:

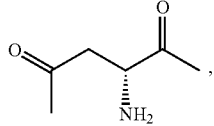
(PI)

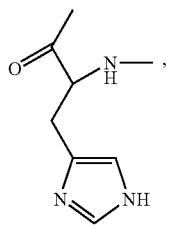
(PII)

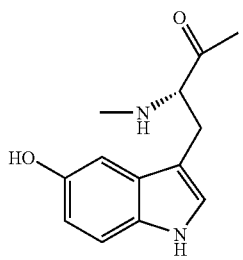
(PIII)

-continued

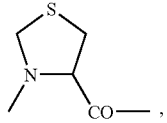
(PIV)

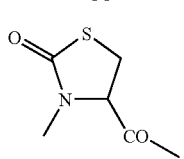
(PV)

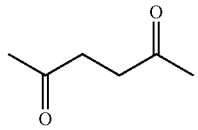
(RI)

$T_C$=(CO) when $T_{B1}$ is X, or
$T_C$=X when $T_{B1}$ is (CO), X being as above defined;
Y is $Y_0$=an alkylenoxy group R'O wherein R' is linear or branched $C_1-C_{20}$ alkyl.

2. A method for the treatment of pathologies associated with stress oxidative and/or endothelial dysfunction comprising administering compounds or salts according to claim 1.

3. Pharmaceutical formulation containing as active principle the compounds or salts thereof of claim 1.

* * * * *